(12) United States Patent
Yamanouchi

(10) Patent No.: US 11,194,033 B2
(45) Date of Patent: *Dec. 7, 2021

(54) OBJECT SENSING DEVICE, AUTOMOTIVE RADAR SYSTEM, SURVEILLANCE RADAR SYSTEM, OBJECT SENSING METHOD, AND PROGRAM

(71) Applicant: NEC Corporation, Tokyo (JP)

(72) Inventor: Shingo Yamanouchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 417 days.

This patent is subject to a terminal disclaimer.

(21) Appl. No.: 16/304,731

(22) PCT Filed: Apr. 21, 2017

(86) PCT No.: PCT/JP2017/016023
§ 371 (c)(1),
(2) Date: Nov. 27, 2018

(87) PCT Pub. No.: WO2017/208670
PCT Pub. Date: Dec. 7, 2017

(65) Prior Publication Data
US 2019/0212429 A1 Jul. 11, 2019

(30) Foreign Application Priority Data
May 30, 2016 (JP) .............................. JP2016-107203

(51) Int. Cl.
*G01S 13/34* (2006.01)
*G01S 13/536* (2006.01)
(Continued)

(52) U.S. Cl.
CPC .......... *G01S 13/34* (2013.01); *A61B 5/02416* (2013.01); *A61B 5/0507* (2013.01);
(Continued)

(58) Field of Classification Search
CPC ........ G01S 13/34; G01S 7/352; G01S 13/343; G01S 13/536; G01S 13/584;
(Continued)

(56) References Cited

U.S. PATENT DOCUMENTS

2008/0074307 A1  3/2008  Boric-Lubecke et al.
2008/0191928 A1  8/2008  Haberland et al.
(Continued)

FOREIGN PATENT DOCUMENTS

EP  2 884 299 A1  6/2015
JP  2007-155396 A  6/2007
(Continued)

OTHER PUBLICATIONS

International Search Report dated Jul. 18, 2017 issued by the International Searching Authority in PCT/JP2017/016023.
(Continued)

*Primary Examiner* — Donald H B Braswell
(74) *Attorney, Agent, or Firm* — Sughrue Mion, PLLC

(57) ABSTRACT

The object sensing device comprises a transmitter and a receiver. The transmitter includes an irradiation unit that irradiates an RF transmission signal having a periodically swept frequency. The receiver includes a reception unit that receives an RF reception signal being a reflected wave of the RF transmission signal reflected by the target, an IF signal generation unit that generates an IF signal by mixing the RF transmission signal with the RF reception signal, a position detection unit that detects a position of the target, based on amplitude of a one-dimensional spectrum calculated from the IF signal for each period in which the frequency is swept, and a displacement detection unit that detects displacement of the target, based on a phase of the one-dimensional spectrum at the detected position of the target.

6 Claims, 19 Drawing Sheets

(51) Int. Cl.
  *G08G 1/16* (2006.01)
  *G01S 7/35* (2006.01)
  *G01S 13/58* (2006.01)
  *G01S 13/931* (2020.01)
  *A61B 5/16* (2006.01)
  *A61B 5/0507* (2021.01)
  *A61B 5/18* (2006.01)
  *A61B 5/00* (2006.01)
  *A61B 5/11* (2006.01)
  *A61B 5/024* (2006.01)

(52) U.S. Cl.
  CPC ............ *A61B 5/1113* (2013.01); *A61B 5/165* (2013.01); *A61B 5/18* (2013.01); *A61B 5/746* (2013.01); *G01S 7/352* (2013.01); *G01S 13/343* (2013.01); *G01S 13/536* (2013.01); *G01S 13/584* (2013.01); *G01S 13/931* (2013.01); *G08G 1/16* (2013.01); *G01S 7/356* (2021.05)

(58) Field of Classification Search
  CPC ............. G01S 13/931; G01S 2007/356; A61B 5/02416; A61B 5/0507; A61B 5/1113; A61B 5/165; A61B 5/18; A61B 5/746; G08G 1/16
  See application file for complete search history.

(56) References Cited

U.S. PATENT DOCUMENTS

| | | | |
|---|---|---|---|
| 2011/0122013 A1 | 5/2011 | Takeya et al. | |
| 2014/0155729 A1 | 6/2014 | Saitoh | |
| 2017/0042432 A1* | 2/2017 | Adib | G01S 7/415 |
| 2018/0368739 A1* | 12/2018 | Zhang | A61B 5/0507 |
| 2019/0279479 A1* | 9/2019 | Reunamaki | A61B 5/1102 |

FOREIGN PATENT DOCUMENTS

| | | |
|---|---|---|
| JP | 2009-510410 A | 3/2009 |
| JP | 2013-80689 A | 5/2013 |
| JP | 5861178 B1 | 2/2016 |
| WO | 2010/134381 A1 | 11/2010 |
| WO | 2011/007828 A1 | 1/2011 |

OTHER PUBLICATIONS

Written Opinion dated Jul. 18, 2017 issued by the International Searching Authority in PCT/JP2017/016023.

Mac Fujimoto and Yusuke Takemoto, A 76/79 GHz band millimeter-wave radar system solution for implementing Advanced Driver Assistance Systems (ADAS), FTF-AUT-F0736, [online], Freescale Technology Forum 2014, [retrieved on Apr. 26, 2016] Internet <URL: http://www.nxp.com/ja/files/FTF-AUT-F0736.pdf?fsrch=1&sr=2&pageNum=1>, 29 pages.

* cited by examiner

OBJECT SENSING DEVICE, AUTOMOTIVE RADAR SYSTEM, SURVEILLANCE RADAR SYSTEM, OBJECT SENSING METHOD, AND PROGRAM

This application is a National Stage Entry of PCT/JP2017/016023 filed on Apr. 21, 2017, which claims priority from Japanese Patent Application 2016-107203 filed on May 30, 2016, the contents of all of which are incorporated herein by reference, in their entirety.

TECHNICAL FIELD

The present invention relates to an object sensing device, an automotive radar system, a surveillance radar system, an object sensing method, and a program.

BACKGROUND ART

An automobile that runs by autonomous driving is developed. For an automobile that runs by autonomous driving, ensuring safety is important. For ensuring safety, a technique of avoiding collision is necessary. In recent years, avoidance of collision with a pedestrian has been drawing attention, especially from a viewpoint of pedestrian protection. For avoiding collision with a pedestrian, detecting a pedestrian correctly is required.

NPL 1 describes, as a related technique, a technique of detecting an object by using a technique of an FMCW scheme or a Fast-FMCW scheme for an automotive radar system.

CITATION LIST

Non-Patent Literature

[NPL 1] Mac Fujimoto and Yusuke Takemoto, A 76/79 GHz band millimeter-wave radar system solution for implementing Advanced Driver Assistance Systems (ADAS), FTF-AUT-F0736, [online], FREESCALE TECHNOLOGY FORUM 2014, [retrieved on Apr. 26, 2016] Internet <URL: http://www.nxp.com/j a/files/FTF-AUT-F0736.pdf?fsrch=1&sr=2&pageNum=1>

SUMMARY OF INVENTION

Technical Problem

Incidentally, when an object is detected by using a technique of, for example, an FMCW scheme or a Fast-FMCW scheme as described in NPL 1, a range resolution is generally about 0.3 m, as described on page 13 and page 15 of NPL 1. This range resolution is due to a fact that a value of a detectable distance is limited to a discrete value for each $c/(2BW)$, because of a characteristic of Fourier transform used in the FMCW scheme or the Fast-FMCW scheme. c is speed of light. BW is a bandwidth of an RF signal. When a BW is 500 MHz, a range resolution becomes 0.3 m. Thus, when an object is detected by using a technique of the FMCW scheme or the Fast-FMCW scheme, a motion that is smaller than the range resolution is undetectable. For example, even when a person moves or a person performs a motion such as waving a hand, the motion may be undetectable, because a range resolution is too coarse in comparison with magnitude of a motion of an object to be detected. As a result, a person is detected as a merely stationary object that does not move or operate, and is not detected as a moving body.

In view of the above, a technique has been required that is able to detect a moving body without using complicated processing or a special device.

An object of the present invention is to provide an object sensing device, an automotive radar system, a surveillance radar system, an object sensing method, and a program that are able to solve the problem described above.

Solution to Problem

To achieve the above object, according to the first aspect of the present invention, an object sensing device comprises a transmitter and a receiver, wherein the transmitter includes an irradiation unit that irradiates an RF transmission signal having a periodically swept frequency, and the receiver includes a reception unit that receives an RF reception signal being a reflected wave of the RF transmission signal reflected by at least one target, an IF signal generation unit that generates an IF signal by mixing the RF transmission signal with the RF reception signal, a position detection unit that detects a position of the target, based on amplitude of a spectrum calculated from the IF signal for each period in which the frequency is swept, and a displacement detection unit that detects displacement of the target, based on a phase of a one-dimensional spectrum at a position of the target being detected by the position detection unit, the phase of the one-dimensional spectrum being calculated from the IF signal for each of the period.

According to the second aspect of the present invention, an object sensing method for an object sensing device including a transmitter and a receiver, comprises: irradiating an RF transmission signal having a periodically swept frequency; receiving an RF reception signal being a reflected wave of the RF transmission signal reflected by at least one target; generating an IF signal by mixing the RF transmission signal with the RF reception signal; detecting a position of the target, based on amplitude of a one-dimensional spectrum calculated from the IF signal for each period in which the frequency is swept; and detecting displacement of the target, based on a phase of the one-dimensional spectrum at a detected position of the target.

According to the third aspect of the present invention, an object sensing method for an object sensing device including a transmitter and a receiver, comprises: irradiating an RF transmission signal having a periodically swept frequency; receiving an RF reception signal being a reflected wave of the RF transmission signal reflected by at least one target; generating an IF signal by mixing the RF transmission signal with the RF reception signal; detecting a position of the target, based on amplitude of a two-dimensional spectrum calculated from the IF signal for each period in which the frequency is swept; calculating a one-dimensional spectrum from the IF signal for each of the period; and detecting displacement of the target, based on a phase of the one-dimensional spectrum at a position of the target being detected from the two-dimensional spectrum.

According to the fourth aspect of the present invention, an automotive radar system comprises: the above object sensing device; and a control device, wherein the object sensing device outputs, to the control device, a position of the target being detected by the position detection unit and displacement of the target being detected by the displacement detection unit, and the control device controls at least one of engine output and braking, based on a position of the target and displacement of the target.

According to the fifth aspect of the present invention, a surveillance radar system comprises: the above object sensing device; and an alarm device, wherein the object sensing device outputs, to the alarm device, displacement of the target being detected by the displacement detection unit, and the alarm device outputs an alarm, based on the displacement.

According to the sixth aspect of the present invention, a program causes a computer of an object sensing device including a transmitter and a receiver, to execute: irradiating an RF transmission signal having a periodically swept frequency;

receiving an RF reception signal being a reflected wave of the RF transmission signal reflected by at least one target; generating an IF signal by mixing the RF transmission signal with the RF reception signal; detecting a position of the target, based on amplitude of a one-dimensional spectrum calculated from the IF signal for each period in which the frequency is swept; and detecting displacement of the target, based on a phase of the one-dimensional spectrum at a detected position of the target.

According to the seventh aspect of the present invention, a program causes a computer of an object sensing device including a transmitter and a receiver, to execute: irradiating an RF transmission signal having a periodically swept frequency; receiving an RF reception signal being a reflected wave of the RF transmission signal reflected by at least one target; generating an IF signal by mixing the RF transmission signal with the RF reception signal; detecting a position of the target, based on amplitude of a two-dimensional spectrum calculated from the IF signal for each period in which the frequency is swept; calculating a one-dimensional spectrum from the IF signal for each of the period; and detecting displacement of the target, based on a phase of the one-dimensional spectrum at a position of the target detected from the two-dimensional spectrum.

Advantageous Effect of Invention

The present invention is able to detect a moving body without using complicated processing or a special device.

EXAMPLE EMBODIMENTS

First Example Embodiment

In the following, example embodiments are described in detail with reference to the drawings.

A configuration of an object sensing device according to a first example embodiment of the present invention is described.

The object sensing device according to the first example embodiment of the present invention is an object sensing device that is a minimum configuration of the present invention.

Figure 1:
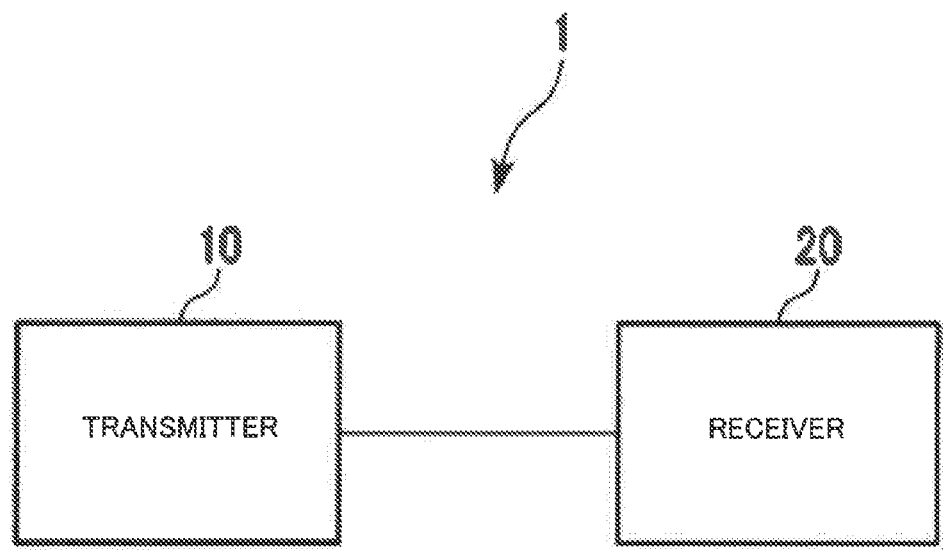
FIG. 1 is a diagram illustrating a minimum configuration of an object sensing device according to a first example embodiment of the present invention.

An object sensing device 1 according to the first example embodiment of the present invention includes a transmitter 10 and a receiver 20, as illustrated in FIG. 1.

Figure 2:
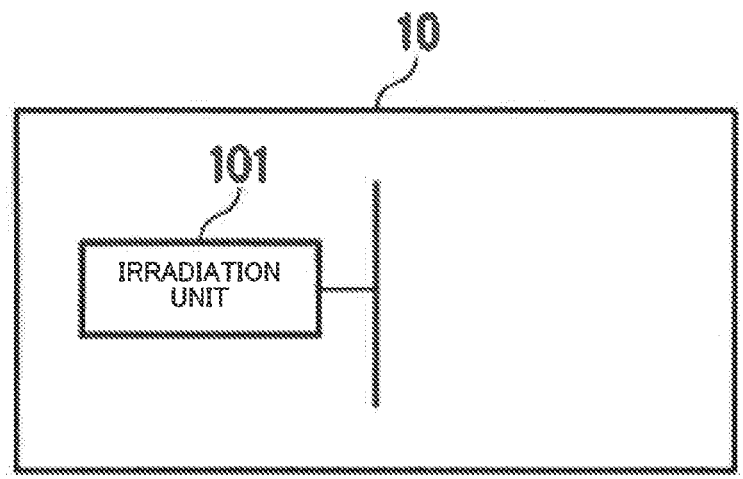
FIG. 2 is a diagram illustrating a configuration of a transmitter according to the first example embodiment of the present invention.

The transmitter 10 includes an irradiation unit 101, as illustrated in FIG. 2.

The irradiation unit 101 irradiates a target with an RF transmission signal having a periodically swept frequency.

Figure 3:
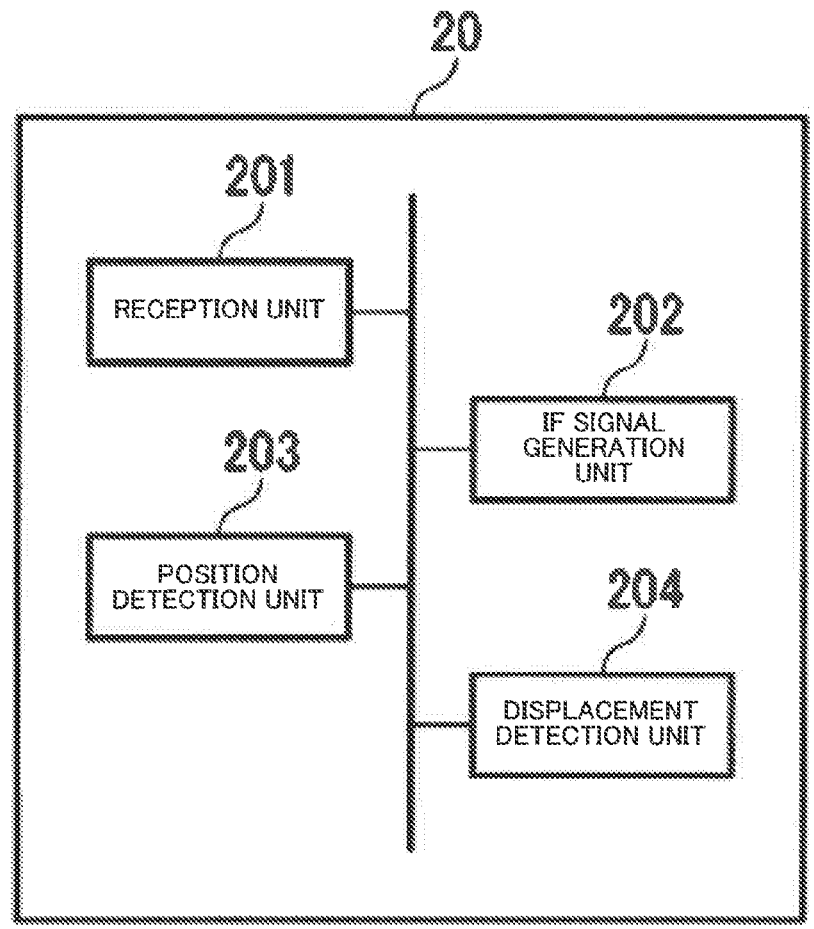
FIG. 3 is a diagram illustrating a configuration of a receiver according to the first example embodiment of the present invention.

The receiver 20 includes a reception unit 201, an IF signal generation unit 202, a position detection unit 203, and a displacement detection unit 204, as illustrated in FIG. 3.

The reception unit 201 receives an RF reception signal that is a reflected wave of the RF transmission signal with which a target is irradiated by the irradiation unit 101.

The IF signal generation unit 202 generates an IF signal by mixing the RF transmission signal with the RF reception signal.

The position detection unit 203 detects a position (a distance between a target and the object sensing device 1) of a target on the basis of a position of a peak in amplitude of a one-dimensional spectrum calculated from an IF signal for each period.

The displacement detection unit 204 detects displacement of a target on the basis of a phase of a one-dimensional spectrum at a position of the target detected by the position detection unit 203.

With such a configuration, the object sensing device 1 is able to determine a displaced target as being a moving body, by detecting a position of a target and detecting displacement of the target at a detected position of the target. As a result, the object sensing device 1 is able to detect a moving body without using complicated processing or a special device.

Second Example Embodiment

A configuration of an object sensing device according to a second example embodiment of the present invention is described.

An object sensing device 1 according to the second example embodiment of the present invention includes a transmitter 10 and a receiver 20, similarly to the object sensing device 1 according to the first example embodiment of the present invention.

Figure 4:
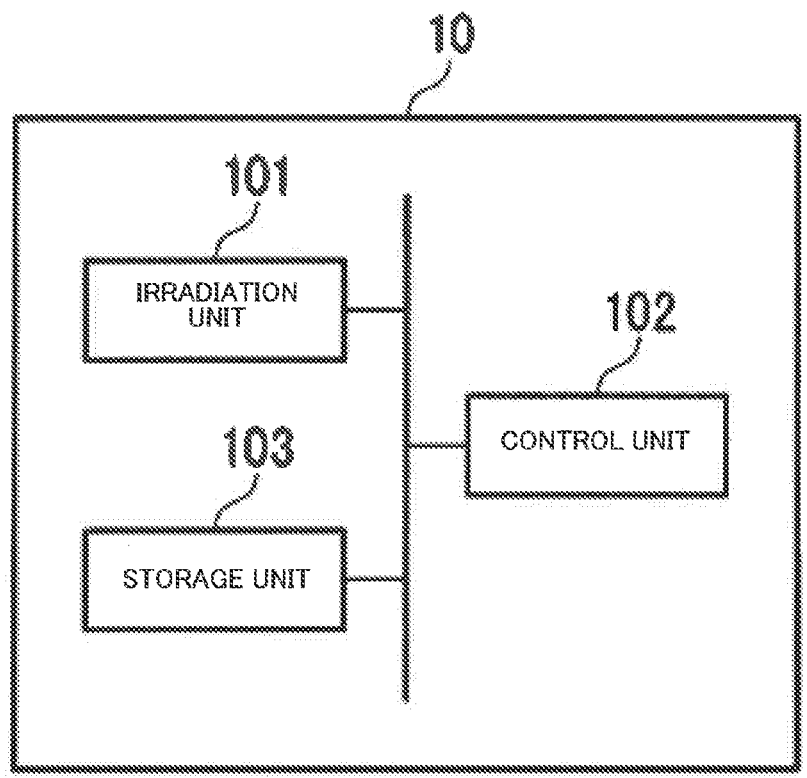
FIG. 4 is a diagram illustrating a configuration of a transmitter according to a second example embodiment of the present invention.

The transmitter 10 includes an irradiation unit 101, a control unit 102, and a storage unit 103, as illustrated in FIG. 4.

The irradiation unit 101 irradiates a target with an RF transmission signal having a periodically swept frequency.

The control unit 102 performs control required for various kinds of processing performed by the transmitter 10.

The storage unit 103 stores various kinds of information required for processing performed by the transmitter 10.

Figure 5:
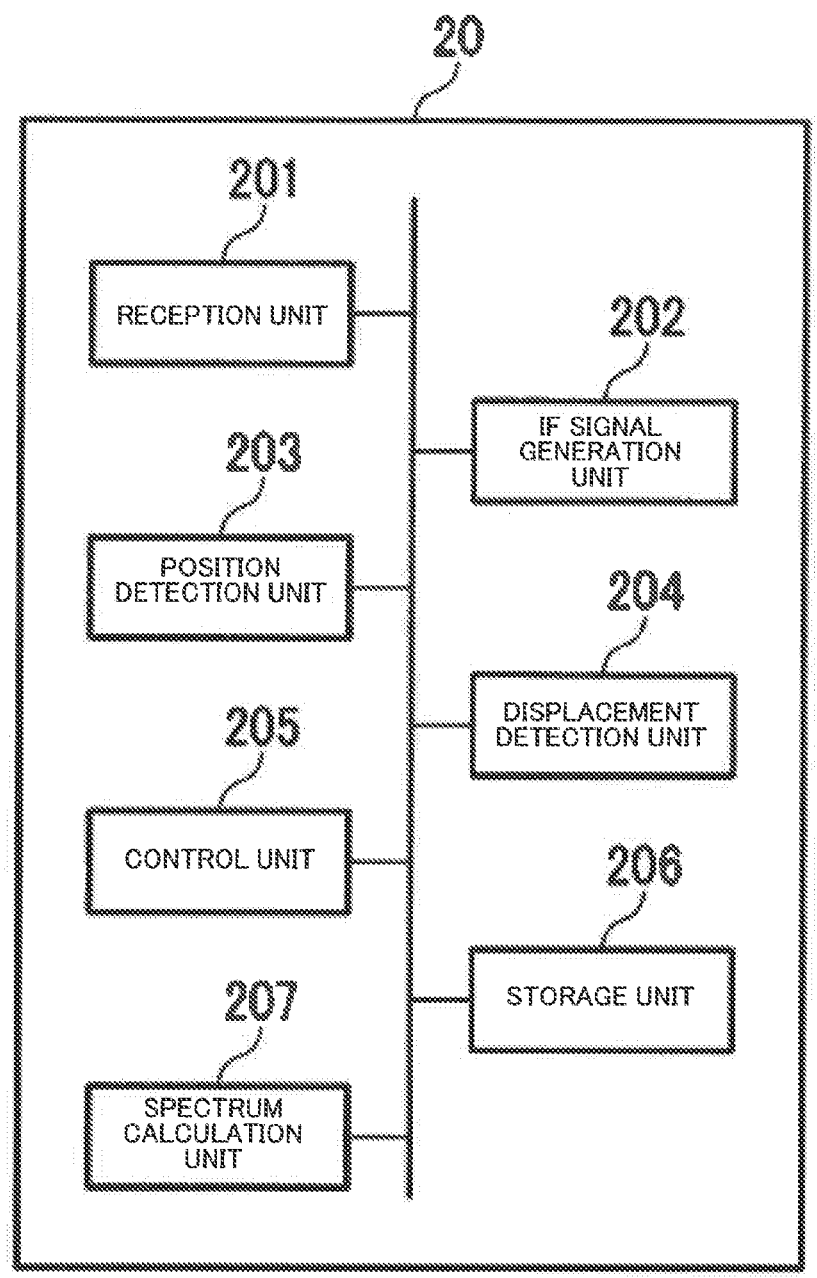
FIG. 5 is a diagram illustrating a configuration of a receiver according to the second example embodiment of the present invention.

The receiver 20 includes a reception unit 201, an IF signal generation unit 202, a position detection unit 203, a displacement detection unit 204, a control unit 205, a storage unit 206, and a spectrum calculation unit 207 (an example of a first spectrum calculation unit and a second spectrum calculation unit), as illustrated in FIG. 5.

The reception unit 201 receives an RF reception signal that is a reflected wave of the RF transmission signal with which a target is irradiated by the irradiation unit 101.

The IF signal generation unit 202 generates an IF signal by mixing the RF transmission signal with the RF reception signal.

The position detection unit 203 detects a position (a distance between a target and the object sensing device 1) R(t) of a target on the basis of a position of a peak in amplitude of a one-dimensional spectrum calculated from an IF signal for each period.

For example, the position detection unit 203 detects, as a position (a distance between a target and the object sensing device 1) $R_0$ of a target at a reference time (t=0), a position of a peak in amplitude of a one-dimensional spectrum $X_r(\omega, k)$ indicated by the later-described Expression (14).

The displacement detection unit 204 detects displacement of a target on the basis of a phase of a one-dimensional spectrum at a position $R_0$ of the target detected by the position detection unit 203.

The control unit 205 performs control required for various kinds of processing performed by the receiver 20.

The storage unit 206 stores various kinds of information required for processing performed by the receiver 20.

The spectrum calculation unit 207 calculates a one-dimensional spectrum $X_r(\omega, k)$ of an IF signal by applying, to the IF signal, one-dimensional Fourier transform for each period.

Processing of the object sensing device according to the second example embodiment of the present invention is described.

Figure 6:
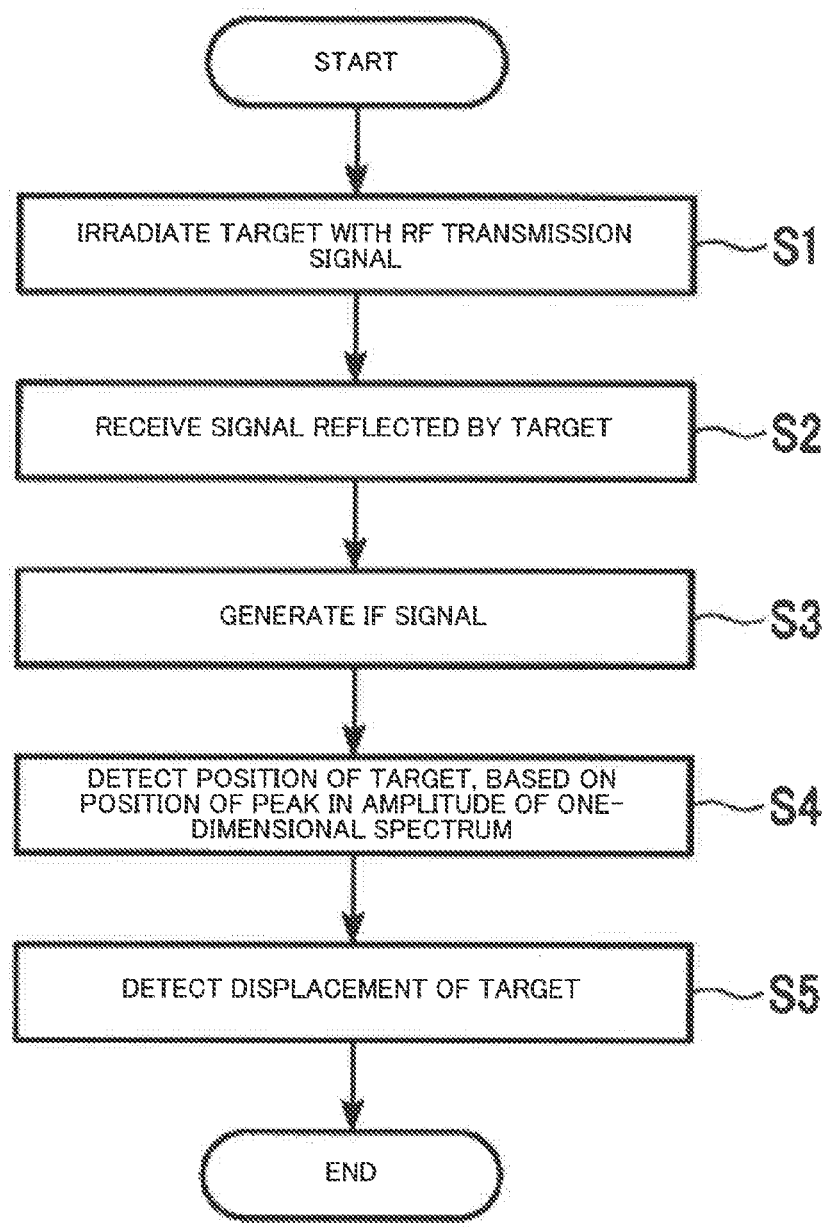
FIG. 6 is a diagram illustrating a processing flow of an object sensing device according to the second example embodiment of the present invention.

Herein, a processing flow of the object sensing device 1 according to the second example embodiment of the present invention illustrated in FIG. 6 is described.

The processing flow of the object sensing device 1 according to the second example embodiment of the present invention illustrated in FIG. 6 is a processing flow in the case of an object-sensing environment with less noise.

The irradiation unit 101 irradiates a target with an RF transmission signal having a swept frequency (Step S1).

For example, an RF transmission signal u(t) is a signal indicated by the following Expression (1).

$$u(t)=U\cos[\theta(t)] \qquad (1)$$

t indicates a time. U indicates amplitude of the RF transmission signal u(t). θ indicates a phase. A phase θ is indicated as a function of a time t.

The RF transmission signal with which the target is irradiated is reflected by the target. The signal reflected by the target returns to the object sensing device 1.

The reception unit 201 receives the signal reflected by the target (Step S2). Hereinafter, the signal received by the reception unit 201, in other words, the signal reflected by the target is referred to as an RF reception signal.

For example, the RF reception signal is a signal indicated by the following Expression (2).

$$u_0(t)=U_0\cos[\theta_0(t)] \qquad (2)$$

$U_0$ indicates amplitude of the RF reception signal $u_0(t)$. $\theta_0(t)$ indicates a phase. A phase $\theta_0(t)$ is indicated as a function of a time t.

The reception unit 201 transmits the received RF reception signal $u_0(t)$ to the IF signal generation unit 202.

The IF signal generation unit 202 acquires the RF transmission signal u(t) from the irradiation unit 101.

Further, the IF signal generation unit 202 acquires the RF reception signal $u_0(t)$ from the reception unit 201.

Figure 7:
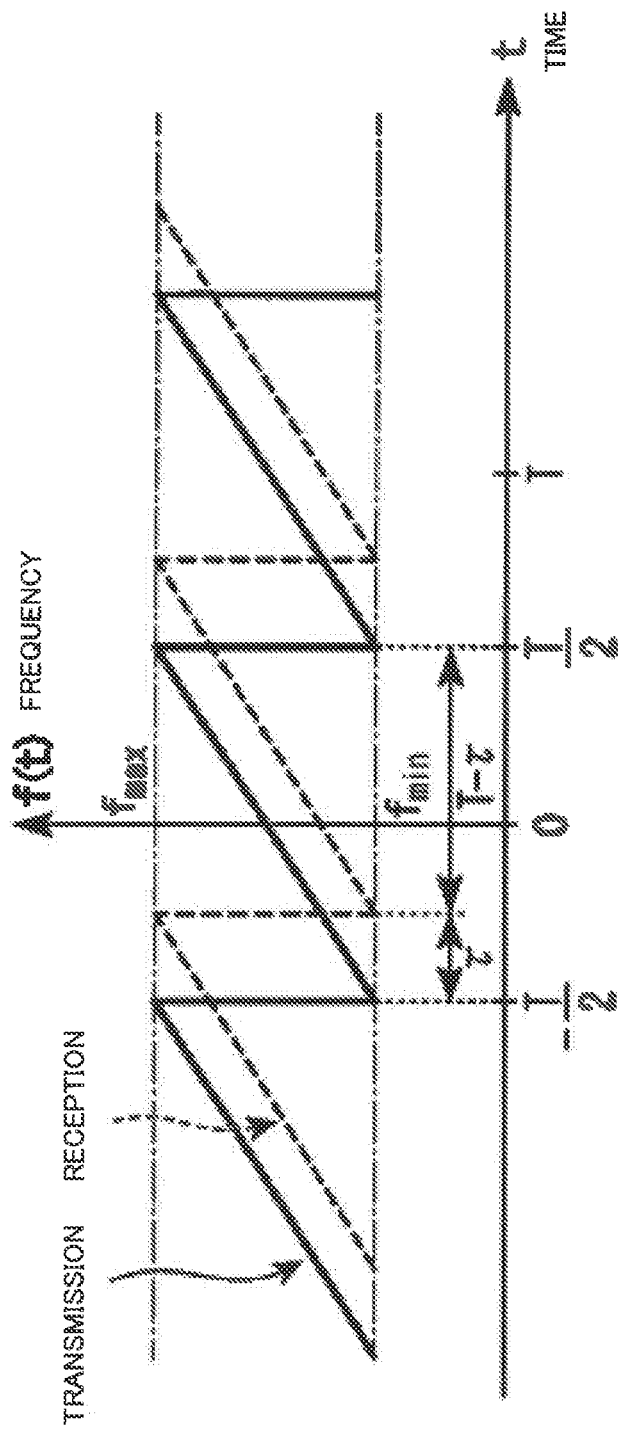
FIG. 7 is a diagram illustrating a chirp signal according to the second example embodiment of the present invention.

The RF transmission signal u(t) acquired by the IF signal generation unit 202 is, for example, a chirp signal illustrated in FIG. 7. It is assumed that a frequency f(t) of a chirp signal changes as indicated in the following Expression (3).

$$f(t)=f_{min}+\alpha(t-kT) \qquad (3)$$

A time t takes a value within a range of (kT−T/2)<t<(kT+T/2). k indicates an integer of 0, ±1, ±2, T indicates one period of a chirp signal. $f_{min}$ indicates a minimum frequency of a chirp signal. α indicates a rate of change (slope) per unit time of a frequency f(t). $f_{max}$ indicates a maximum frequency of a chirp signal.

When a frequency f(t) of the RF transmission signal u(t) changes as indicated in Expression (3), a relation indicated in the following Expression (4) holds between a frequency f(t) and a phase θ(t).

$$f(t) = (1/(2\pi)) \times (d\theta(t)/dt) \quad (4)$$

From Expressions (3) and (4), a phase θ(t) is calculated as indicated in the following Expression (5).

$$\theta(t_k) = 2\pi f_{min} t_k + \pi \alpha t_k^2 \quad (5)$$

Herein, $t_k = t - kT$, and $t - kT$ is replaced with $t_k$.

When the RF reception signal $u_0(t)$ acquired by the IF signal generation unit 202 is, for example, the chirp signal illustrated in FIG. 7, a delay time T occurs between the RF transmission signal $u(t)$ and the RF reception signal $u_0(t)$.

At this time, a relation of a phase indicated in the following Expression (6) holds.

$$\theta_0(t) = \theta(t-T) \quad (6)$$

Since $R(t) = R_0 + vt$ and $\tau_0 = 2R_0/c$, the delay time T is separated as indicated in the following Expression (7).

$$\tau = 2R(t)/c = \tau_0 + 2vt/c \quad (7)$$

To in Expression (7) is a delay time of an RF reception signal $u_0(0)$ with respect to an RF transmission signal $u(0)$ output at a reference time t=0. v is a velocity at which a target moves. c is speed of light.

$2vt/c$ that is the second term on the right side in Expression (7) indicates change in a delay time of the RF reception signal $u_0(t)$ with respect to the RF transmission signal $u(t)$ when a target moves at a velocity v.

Note that a relation indicated by the following Expression (8) holds between a delay time $\tau_0$ and a position $R_0$ of a target at a time t=0.

$$\tau_0 = 2R_0/c \quad (8)$$

The IF signal generation unit 202 generates an IF signal by mixing the acquired RF transmission signal $u(t)$ with the acquired RF reception signal $u_0(t)$ (Step S3).

Specifically, the IF signal generation unit 202 generates, for example, an IF signal x(t) indicated in the following Expression (9).

$$x(t) = \cos[\theta_w(t)] \quad (9)$$

A phase $\theta_w(t)$ of an IF signal x(t) is a phase indicated in the following Expression (10).

$$\theta_w(t) = \theta(t) - \theta_0(t) \quad (10)$$
$$= 2\pi f_{min}\tau - \pi\alpha(\tau^2 - 2t_k\tau)$$

$\theta_w(t)$ indicated by Expression (10) is a value when a time $t_k$ is within a range of $(-T/2+\tau) < t_k < (T/2)$.

When a position (a distance from the object sensing device 1 to a target) R(t) of a target is 60 m, a delay time is τ=0.4 u seconds. Further, a representative value of a time $t_k$ is a chirp period T (about 100 u seconds). Therefore, when a delay time τ and a time $t_k$ in Expression (10) are compared, the delay time τ is sufficiently small in comparison with the time $t_k$.

In view of the above, when a condition of delay time τ<<time $t_k$ is applied in Expression (10), approximation that ignores a term of $\tau^2$ is possible.

With this approximation, a phase θw(t) of an IF signal x(t) is indicated as in the following Expression (11).

$$\theta w(t) = 2\pi[f_{min}\tau_0 + kf_dT + (f_w + f_d)t_k] \quad (11)$$

$f_d$ in Expression (11) is a Doppler frequency. $f_w$ is a frequency shift generated from a delay time $\tau_0$ at a position $R_0$ of a target.

A Doppler frequency $f_d$ may be represented as in the following Expression (12).

$$f_d = 2v f_{min}/c \quad (12)$$

A frequency shift $f_w$ may be represented as in the following Expression (13).

$$f_w = \alpha \tau_0 \quad (13)$$

The spectrum calculation unit 207 performs one-dimensional Fourier transform on an IF signal x(t) for a period T of a chirp signal. A one-dimensional spectrum (complex spectrum) $X_r(\omega, k)$ calculated by the spectrum calculation unit 207 may be represented as in the following Expression (14).

[Mathematical 1]

$$X_r(\omega, k) \approx \int_{-T/2}^{T/2} x(t_k) \exp(-j\omega t_k) dt_k = \quad (14)$$
$$\frac{2\exp[j2\pi(f_{min}\tau_0 + kf_d T)]}{2\pi(f_w + f_d) - \omega} \sin\left[\{2\pi(f_w + f_d) - \omega\}\frac{T}{2}\right]$$

A lower end of an integral interval in Expression (14) is originally $(-T/2)+\tau$. However, since period T>>delay time τ, the lower end of the integral interval is approximated to $(-T/2)$.

The position detection unit 203 detects a position R(t) of the target on the basis of a position of a peak in amplitude of the one-dimensional spectrum $X_r(\omega, k)$ calculated by the spectrum calculation unit 207 from the IF signal x(t) for each period (Step S4).

For example, the position detection unit 203 detects, as a position R(t) of the target, a position of a peak in amplitude of the one-dimensional spectrum $X_r(\omega, k)$ indicated by Expression (14).

When the number of chirps is K, a phase $\angle X_r(\omega, k)$ of a one-dimensional spectrum $X_r(\omega, k)$ indicated by Expression (14) may be represented as in the following Expression (15).

[Mathematical 2]

$$\angle X_r(\omega, k) = 2\pi(f_{min}\tau_0 + kf_d T), \quad (15)$$
$$= \frac{4\pi}{\lambda}(R_0 + vkT) \equiv \frac{4\pi}{\lambda}(R_0 + a(kT)) \equiv \frac{4\pi}{\lambda}R(kT),$$

k in Expression (15) is an integer of 0, 1, 2, ..., K. a(kT) represents displacement (shaking/vibration) from an initial position $R_0$. R(kT) represents a position (a distance between a target and the object sensing device 1) of a target measured for each period T of a chirp signal.

The displacement detection unit 204 detects displacement a(kT) of the target on the basis of a phase $\angle X_r(\omega, k)$ of the one-dimensional spectrum at the position $R_0$ of the target detected by the position detection unit 203 (Step S5).

From Expression (15), a position R(t) of a target may be represented as in the following Expression (16).

$$R(kT) = (R_0 + a(kT)) \quad (16)$$

A distance R(t) of a target specified from a phase $\angle X_r(\omega, k)$ of a one-dimensional spectrum has two properties (a) and (b) indicated below.

(a) An absolute value of a distance R(t) of a target specified from a phase ∠$X_r$(ω, k) of a one-dimensional spectrum cannot be obtained.

(b) A resolution of displacement obtained from temporal change in a distance R(t) of a target is not restricted by a range resolution c/(2BW) according to one-dimensional Fourier transform performed when calculating a one-dimensional spectrum $X_r$(0), k).

The property (a) of a distance R(t) of a target is described.

A phase ∠$X_r$(ω, k) of a one-dimensional spectrum is treated equally between the cases where an inconstant constant (a phase that is integer multiple of 2n) is added and not added. Thus, even when an inconstant constant is added to the right side of a phase ∠$X_r$(ω, k) of a one-dimensional spectrum represented by Expression (15), it is impossible to determine, from a measured value of the phase ∠$X_r$(ω, k), whether or not an inconstant constant is added.

Therefore, the displacement detection unit 204 is unable to specify an absolute value of a distance R(t) represented by Expression (16) obtained from a phase ∠$X_r$(ω, k) of a one-dimensional spectrum.

However, the displacement detection unit 204 is able to correctly specify displacement (shaking/vibration) a(kT) of a target excluding an inconstant constant from temporal change in a distance R(t). In other words, the displacement detection unit 204 is able to determine whether or not displacement of a target is detected, according to presence or absence of temporal change in a distance R(t) of the target for each period of an IF signal x(t) indicated by a phase of a one-dimensional spectrum. The displacement detection unit 204 determines that displacement of a target is detected, when there is temporal change in a distance R(t) of the target for each period of an IF signal x(t) indicated by a phase of a one-dimensional spectrum. Further, the displacement detection unit 204 determines that displacement of a target is not detected, when there is no temporal change in a distance R(t) of the target for each period of an IF signal x(t) indicated by a phase of a one-dimensional spectrum.

In other words, the displacement detection unit 204 detects presence or absence of displacement of a target, from a phase of a one-dimensional spectrum of each IF signal x(t) obtained for each period of a chirp signal.

The property (b) of a distance R(t) of a target is described.

When a distance R(t) is specified from a phase ∠$X_r$(ω, k) of a one-dimensional spectrum, a resolution of the distance R(t) is restricted by a phase error, not by a range resolution c/(2BW) according to one-dimensional Fourier transform performed when calculating a one-dimensional spectrum $X_r$(ω, k).

A phase ∠$X_r$(ω, k) of a one-dimensional spectrum in the case of including a phase error may be represented as in the following Expression (17).

[Mathematical 3]

$$\angle X_r(\omega, k) = \frac{4\pi}{\lambda} R(t) + \Delta\theta = \frac{4\pi}{\lambda}\left[R(t) + \frac{\lambda}{4\pi}\Delta\theta\right] \quad (17)$$

Δθ in Expression (17) is a phase error.

As can be understood from Expression (17), an error ΔR of a distance generated from a phase error Δθ may be represented as in the following Expression (18).

$$\Delta R = (\lambda/4\pi) \times \Delta\theta \quad (18)$$

λ in Expression (18) is a wavelength of $f_{min}$. For example, when a wavelength λ is 4 mm ($f_{min}$=75 GHz) and a phase error Δθ is 3°, an error ΔR of a distance is 17 um, from Expression (18).

In other words, the position detection unit 203 is able to specify displacement of a target at a high resolution on the basis of a phase ∠$X_r$(ω, k) of a one-dimensional spectrum.

Note that displacement of a target specified by the position detection unit 203 is a distance R(t) direction (a direction from the object sensing device 1 toward a target, or a direction from a target toward the object sensing device 1). The position detection unit 203 does not specify displacement of a target in an angle direction (a direction other than a distance R(t) direction).

Figure 8:
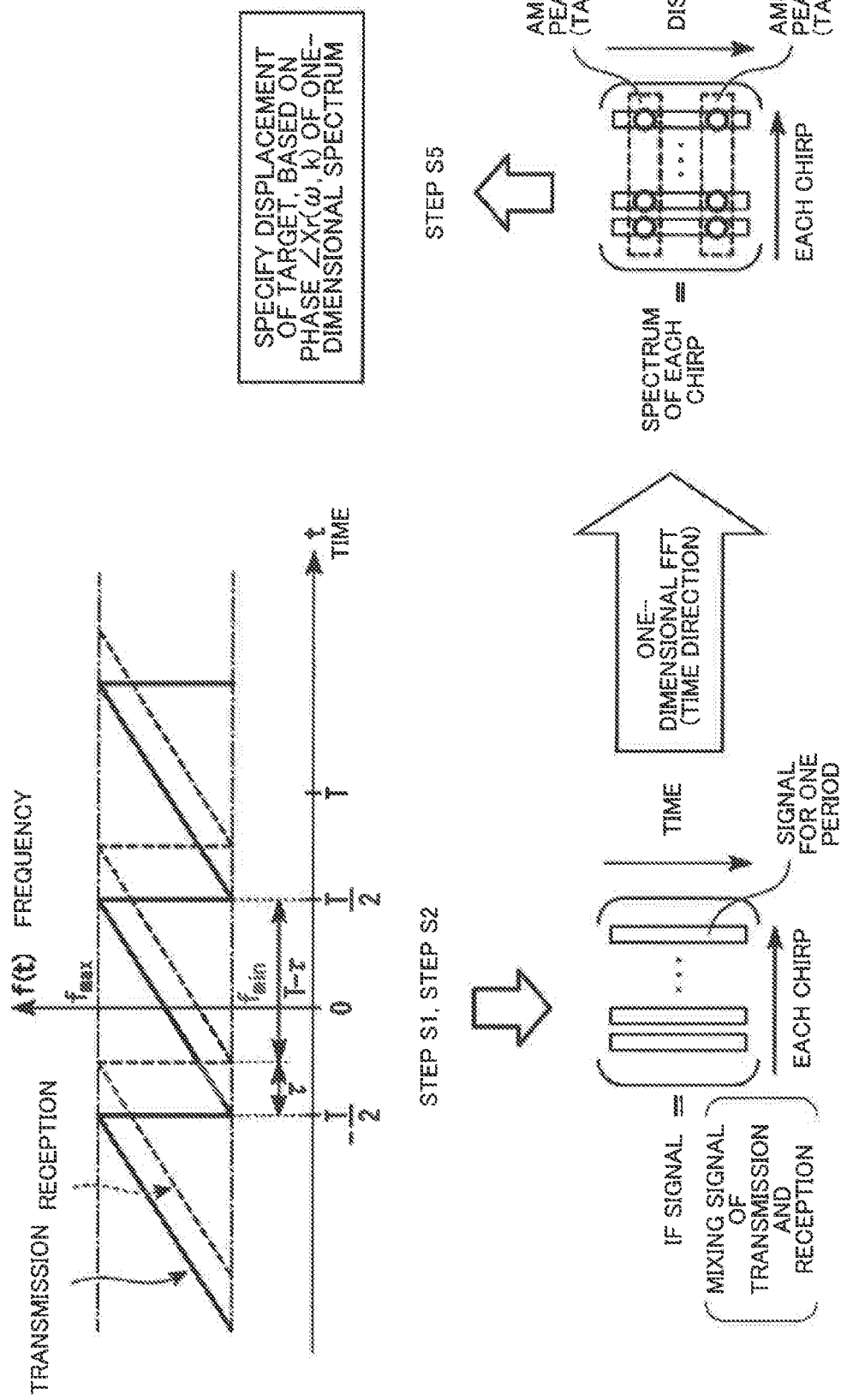
FIG. 8 is an image illustrating processing of the object sensing device according to the second example embodiment of the present invention.

In summary, the processing of the object sensing device 1 according to the second example embodiment of the present invention described above may be represented as in an image illustrated in FIG. 8.

The object sensing device 1 irradiates a target with the RF transmission signal u(t) having a swept frequency and receives a reception signal $u_0$(t) reflected by the target, through the processing of Steps S1 and S2.

The object sensing device 1 generates an IF signal by mixing the RF transmission signal u(t) with the reception signal $u_0$(t), through the processing of Step S3.

The object sensing device 1 specifies, as a position $R_0$ of the target, a position of a peak in amplitude of a one-dimensional spectrum $X_r$(ω, k) obtained by performing one-dimensional Fourier transform on the IF signal x(t), through the processing of Step S4. Through this processing of Step S4, the object sensing device 1 is deemed as specifying a position of the target at a position resolution of about 30 cm. A position $R_0$ of the target is obtained for each period of a chirp signal, in other words, for each one-dimensional spectrum of each period.

The object sensing device 1 specifies displacement of the target on the basis of a phase ∠$X_r$(ω, k) of the one-dimensional spectrum at the position $R_0$ of the target, through the processing of Step S5. Through this processing of Step S5, the object sensing device 1 is deemed as determining whether or not there is displacement in the target, in other words, whether or not the target is a moving body.

Note that each functional unit may be a unit that stores an expression required for processing. Further, a storage unit may store an expression, and each functional unit may read a required expression from the storage unit.

In the above, the object sensing device 1 according to the second example embodiment of the present invention has been described. The object sensing device 1 according to the second example embodiment of the present invention includes the transmitter 10 and the receiver 20. The transmitter 10 includes the irradiation unit 101, the control unit 102, and the storage unit 103. The irradiation unit 101 irradiates, for each period T, a target with the RF transmission signal u(t) having a periodically swept frequency. The control unit 102 performs control required for various kinds of processing performed by the transmitter 10. The storage unit 103 stores various kinds of information required for processing performed by the transmitter 10. The receiver 20 includes the reception unit 201, the IF signal generation unit 202, the position detection unit 203, the displacement detection unit 204, the control unit 205, the storage unit 206, and the spectrum calculation unit 207. The reception unit 201 receives the RF reception signal $u_0$(t) that is a reflected wave of the RF transmission signal u(t) with which a target is irradiated by the irradiation unit 101. The IF signal generation unit 202 generates an IF signal x(t) by mixing the RF transmission signal u(t) with the RF reception signal $u_0(t)$. The spectrum calculation unit 207 calculates a one-dimensional spectrum $X_r(\omega, k)$ of an IF signal x(t) by applying one-dimensional Fourier transform for each period. The position detection unit 203 detects a position $R_0$ of a target on the basis of a position of a peak in amplitude of a one-dimensional spectrum $X_r(\omega, k)$ calculated from an IF signal x(t) for each period. The displacement detection unit 204 specifies a distance R(t) on the basis of a phase $\angle X_r(\omega, k)$ of a one-dimensional spectrum $X_r(\omega, k)$ at a position $R_0$ of a target detected by the position detection unit 203. The displacement detection unit 204 senses displacement (shaking/vibration) of a target excluding an inconstant constant from temporal change in a distance R(t). The control unit 205 performs control required for various kinds of processing performed by the receiver 20. The storage unit 206 stores various kinds of information required for processing performed by the receiver 20.

With such a configuration, the object sensing device 1 is able to detect a moving body without using complicated processing or a special device.

Third Example Embodiment

A configuration of an object sensing device according to a third example embodiment of the present invention is described.

An object sensing device 1 according to the third example embodiment of the present invention includes a transmitter 10 and a receiver 20, similarly to the object sensing device 1 according to the second example embodiment of the present invention.

The transmitter 10 includes an irradiation unit 101, a control unit 102, and a storage unit 103, similarly to the transmitter 10 according to the second example embodiment illustrated in FIG. 4.

The receiver 20 includes a reception unit 201, an IF signal generation unit 202, a position detection unit 203, a displacement detection unit 204, a control unit 205, a storage unit 206, and a spectrum calculation unit 207, similarly to the receiver 20 according to the second example embodiment illustrated in FIG. 5.

The spectrum calculation unit 207 calculates a two-dimensional spectrum $X(\omega, \Psi)$ of an IF signal x(t) by applying two-dimensional Fourier transform for each period. The spectrum calculation unit 207 calculates a one-dimensional spectrum $X_r(\omega, k)$ of an IF signal x(t) by applying one-dimensional Fourier transform for each period.

The position detection unit 203 detects a position $R_0$ of a target on the basis of a position of a peak in amplitude of a two-dimensional spectrum calculated from an IF signal for each period.

For example, the position detection unit 203 detects, as a position $R_0$ of a target, a position of a peak in amplitude of a two-dimensional spectrum $X(\omega, \Psi)$ calculated by the spectrum calculation unit 207.

Processing of the object sensing device according to the third example embodiment of the present invention is described.

Figure 9:
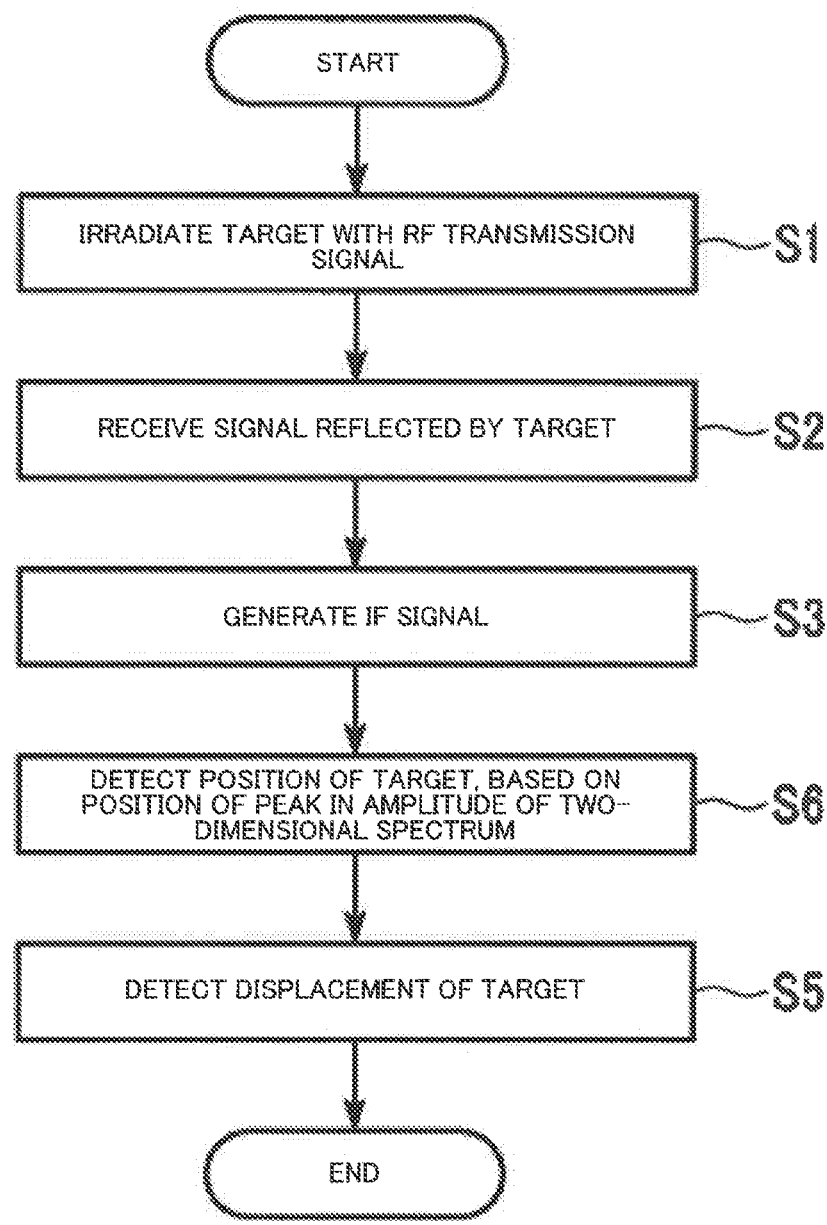
FIG. 9 is a diagram illustrating a processing flow of an object sensing device according to a third example embodiment of the present invention.

Herein, a processing flow of the object sensing device 1 according to the third example embodiment of the present invention illustrated in FIG. 9 is described.

The processing flow of the object sensing device 1 according to the third example embodiment of the present invention illustrated in FIG. 9 is a processing flow in the case of an object-sensing environment with much noise.

The object sensing device 1 performs processing of Steps S1 to S3.

The position detection unit 203 detects a position $R_0$ of a target on the basis of a position of a peak in amplitude of a two-dimensional spectrum $X(\omega, \Psi)$ calculated by the spectrum calculation unit 207 (Step S6). A two-dimensional spectrum $X(\omega, \Psi)$ is obtained by two-dimensional Fourier transform on a matrix that has a plurality of column vectors indicating an IF signal x(t) for each period of a chirp signal.

For example, the position detection unit 203 detects, as a position $R_0$ of a target, a position of a peak in amplitude of a two-dimensional spectrum $X(\omega, \Psi)$ indicated by the following Expression (19).

An SN ratio according to a method in which the position detection unit 203 detects a position $R_0$ of a target on the basis of a position of a peak in amplitude of a two-dimensional spectrum $X(\omega, \Psi)$ is improved by $10 \log_{10}(K)$ decibel when the number of chirps is K, in comparison with an SN ratio according to a method in which the position detection unit 203 detects a position $R_0$ of a target on the basis of a position of a peak in amplitude of a one-dimensional spectrum $X_r(\omega, k)$.

[Mathematical 4]

$$X(\omega, \psi) = \sum_{k=0}^{K-1} X_r(\omega, k)\exp(-jk\psi) \qquad (19)$$
$$= \frac{2\exp(j2\pi f_{min}\tau_0)}{2\pi(f_w + f_d) - \omega} \cdot \frac{\exp[jK(2\pi f_d T - \psi)] - 1}{\exp[j(2\pi f_d T - \psi)] - 1}$$

K in Expression (19) is the number of chirps. A two-dimensional spectrum $X(\omega, \Psi)$ is a two-dimensional spectrum obtained by performing two-dimensional Fourier transform on an IF signal x(t) for a period T of a chirp signal, and may be represented by using a one-dimensional spectrum $X_r(\omega, k)$.

In $\omega = 2\pi(f_w + f_d) \approx 2\pi f_w T$ and in which a denominator of a two-dimensional spectrum $X(\omega, \Psi)$ becomes 0 (zero), amplitude $|X(\omega, \Psi)|$ of two-dimensional Fourier transform has a peak.

Therefore, from a peak in amplitude $|X(\omega, \Psi)|$ of two-dimensional Fourier transform, frequencies $f_w(=aR_0/c)$ and $f_d(=2vf_{min}/c)$ are obtained, and the position detection unit 203 is able to calculate, from the frequencies $f_w$ and $f_d$, a position $R_0$ and a velocity v of a target at a time t=0. In step S6 shown in FIG. 9, the position detection unit 203 may obtain not only the position R0 of the object but also the velocity v as described above.

An argument $\omega$ of a two-dimensional spectrum $X(\omega, \Psi)$ is proportional to a position $R_0$ of a target, and an argument $\Psi$ is proportional to a velocity v. Thus, by performing scale transform on a two-dimensional spectrum $X(\omega, \Psi)$ and replacing arguments $(\omega, \Psi)$ of amplitude $|X(\omega, \Psi)|$ of two-dimensional Fourier transform with a position $R_0$ and a velocity v of a target, a two-dimensional plot using, for example, a position $R_0$ and a velocity v illustrated in FIG. 10 as axes may be obtained.

The displacement detection unit 204 detects, through processing of Step S5, displacement of the target on the basis of a phase $\angle Xr(\omega, \Psi)$ of a two-dimensional spectrum at the position $R_0$ and the velocity v of the target detected by the position detection unit 203 (Step S5).

Figure 10:
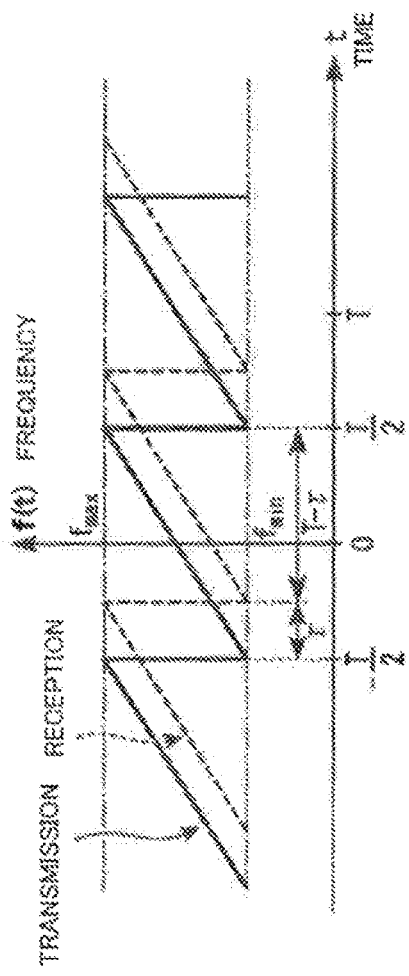
FIG. 10 is an image illustrating processing of the object sensing device according to the third example embodiment of the present invention.

In summary, the processing of the object sensing device 1 according to the third example embodiment of the present invention described above may be represented as in an image illustrated in FIG. 10.

The object sensing device 1 irradiates a target with the RF transmission signal u(t) having a swept frequency and receives a reception signal $u_0(t)$ reflected by the target, through the processing of Steps S1 and S2.

The object sensing device 1 generates an IF signal by mixing the RF transmission signal u(t) with the reception signal $u_0(t)$, through the processing of Step S3.

The object sensing device 1 detects a position $R_0$ and the velocity v of the target on the basis of a position of a peak in amplitude of a two-dimensional spectrum $X(\omega, \Psi)$, through the processing of Step S6. Through this processing of Step S6, the object sensing device 1 1 is deemed as specifying a position of the target at a position and the velocity resolution of about 30 cm.

The object sensing device 1 specifies displacement of the target on the basis of a phase $\angle Xr(\omega, \Psi)$ of a two-dimensional spectrum at the position $R_0$ and the velocity v of the target, through the processing of Step S5. Through this processing of Step S5, the object sensing device 1 is deemed as determining whether or not there is displacement in the target, in other words, whether or not the target is a moving body.

Note that each functional unit may be a unit that stores an expression required for processing. Further, a storage unit may store an expression, and each functional unit may read a required expression from the storage unit.

(Simulation Example)

A simulation example is described.

A displacement detection performance was verified by simulation respectively for the case of performing displacement measurement after detecting a position of a target by using one-dimensional Fourier transform as in the second example embodiment of the present invention, and for the case of performing displacement measurement after detecting a position of a target by using two-dimensional Fourier transform as in the third example embodiment of the present invention. In the simulation, a parameter of a simulator is set in such a manner that a target T1 is present at a position 100 m distant from the object sensing device 1, and that a target T2 is present at a position 20 m distant from the object sensing device 1. Further, the target T1 is assumed to be a car, and a parameter of the simulator is set in such a manner that a whole automobile vibrates at an amplitude of 1 cm and a frequency of 10 Hz in a direction indicating a distance between the object sensing device 1 and the target. Further, the target T2 is assumed to be a pedestrian, and a parameter of the simulator is set in such a manner that a whole body of the pedestrian moves at an amplitude of 10 cm and a frequency of 1 Hz in a direction indicating a distance between the object sensing device 1 and the target.

Figure 11:
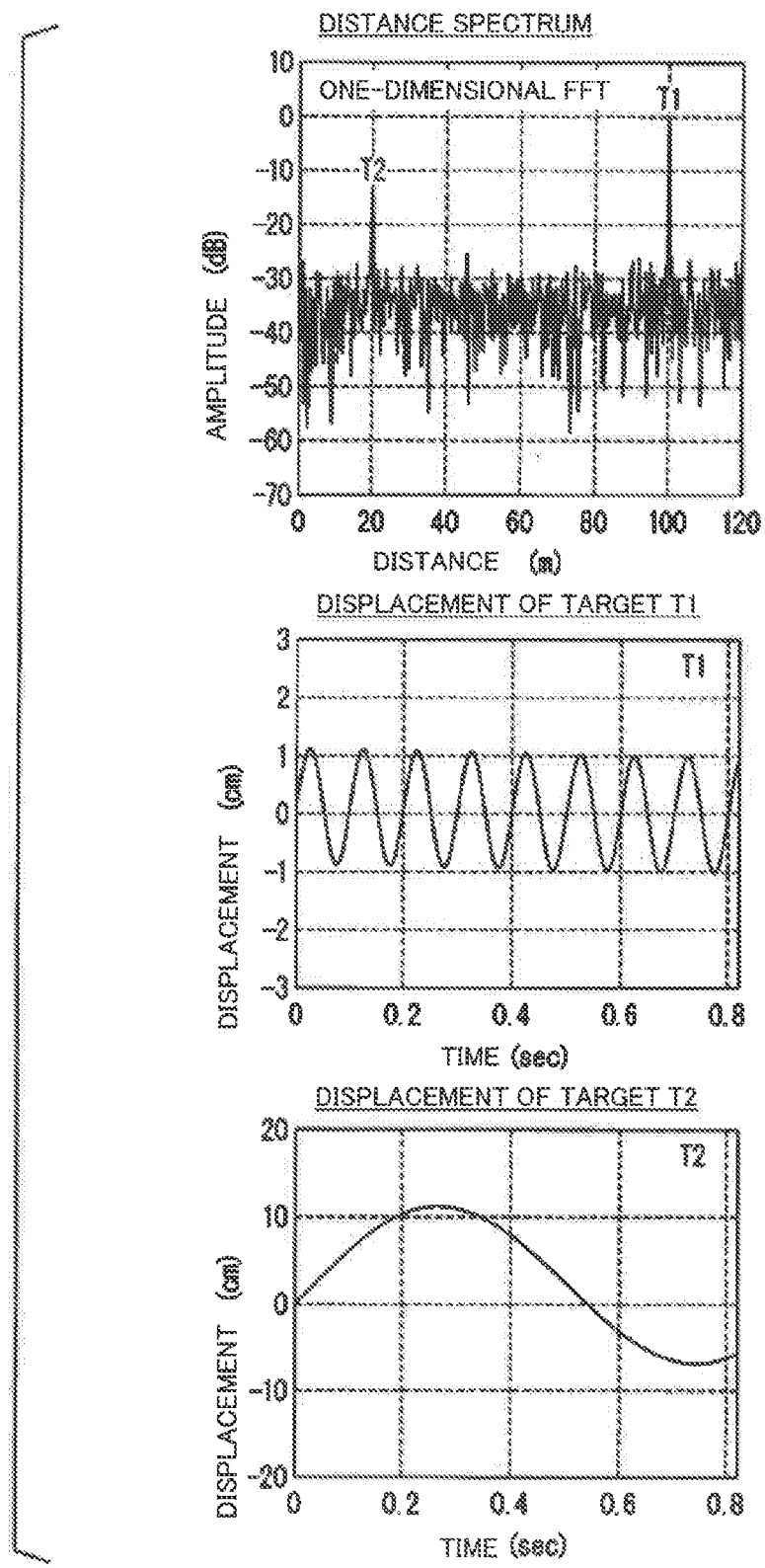
FIG. 11 is a first diagram illustrating a simulation result according to the second example embodiment of the present invention.

FIG. 11 illustrates a simulation result in the case of respectively sensing a position (distance) and displacement of the targets T1 and T2 in accordance with the procedure indicated in the second example embodiment of the present invention. As a simulation result, a spectrum, displacement of the target T1, and displacement of the target T2 are illustrated. As illustrated in FIG. 11, it can be seen that a position and displacement (vibration) of each of the targets T1 and T2 are detected, by the object sensing device 1 indicated in the second example embodiment of the present invention, at values as in set arrangement.

Figure 12:
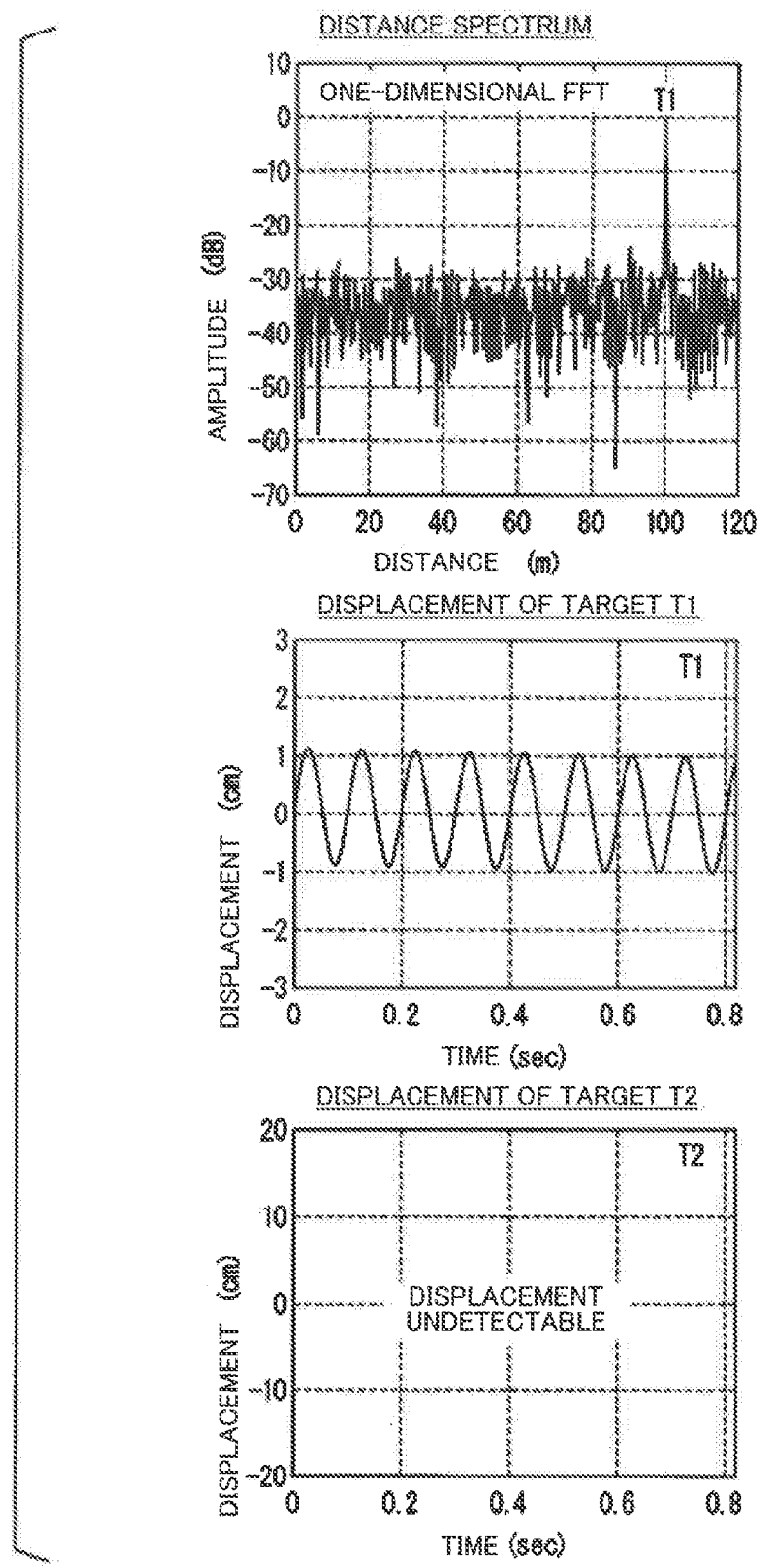
FIG. 12 is a second diagram illustrating a simulation result according to the second example embodiment of the present invention.

Next, the position of the target T2 was changed from 20 m to 50 m, and a simulation similar to the above-described simulation was performed. FIG. 12 illustrates a simulation result in the case of respectively sensing a position (distance) and displacement of the targets T1 and T2 in accordance with the procedure indicated in the second example embodiment of the present invention. As a simulation result, a spectrum, displacement of the target T1, and displacement of the target T2 are illustrated. In a distance spectrum illustrated in FIG. 12, an amplitude peak of the target T2 is buried in a noise floor and cannot be sensed. Thus, a position or presence of the target T2 cannot be sensed, which results in failing to sense displacement of the target T2.

Figure 13:
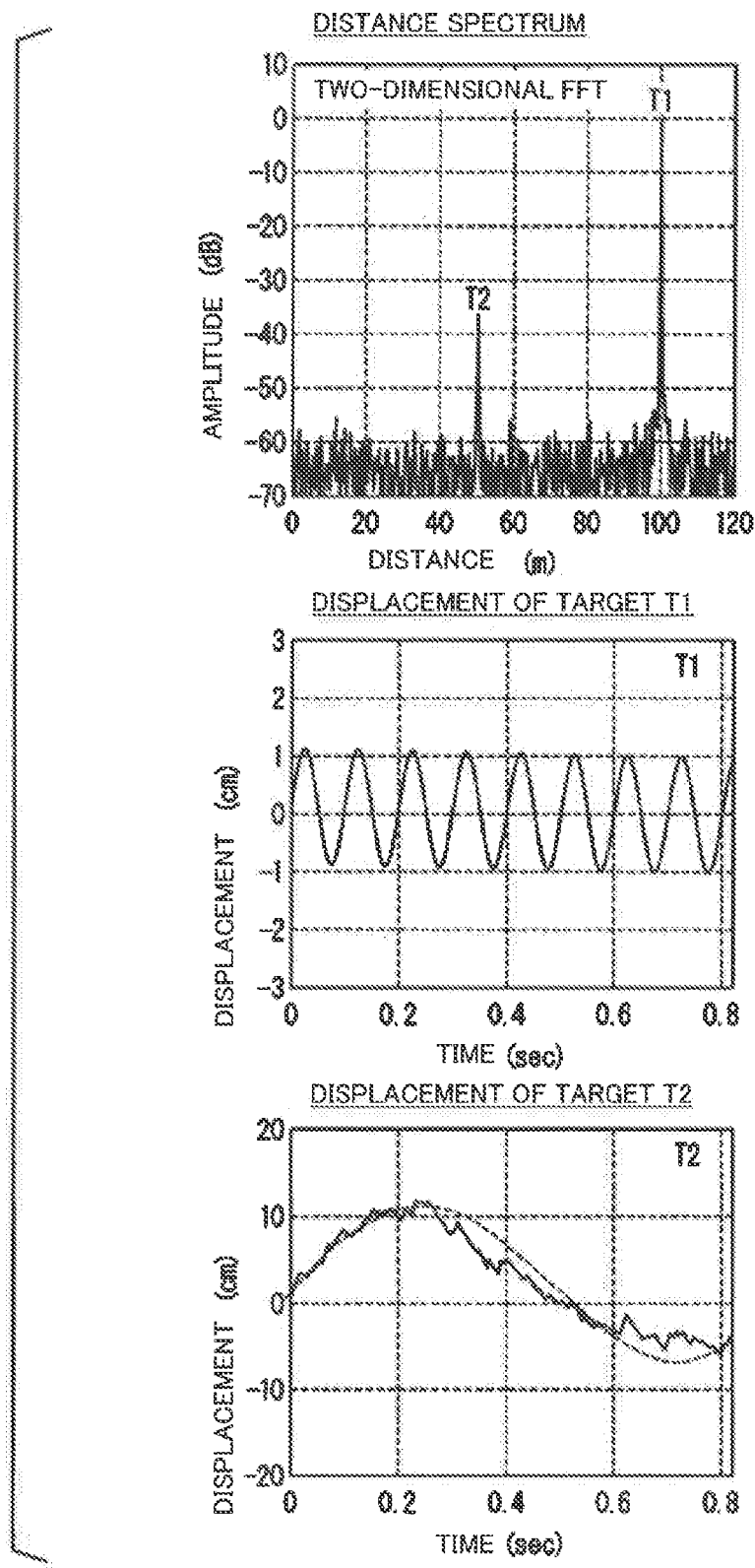
FIG. 13 is a diagram illustrating a simulation result according to the third example embodiment of the present invention.

Next, FIG. 13 illustrates a result of respectively sensing a position (distance) and displacement of the targets T1 and T2, with the position of the target T2 still being kept at 50 m, in accordance with the procedure indicated in the third example embodiment of the present invention. As a simulation result, a spectrum, displacement of the target T1, and displacement of the target T2 are illustrated. In a distance spectrum illustrated in FIG. 13, a noise floor is lowered and an amplitude peak of the target T2 is successfully sensed. This is an advantageous effect of the fact that, as described above, an SN ratio according to a method of detecting a position $R_0$ of a target on the basis of a position of a peak in amplitude of a two-dimensional spectrum $X(\omega, \Psi)$ is improved by $10 \log_{10}(K)$ decibel, in comparison with an SN ratio according to a method of detecting a position $R_0$ of a target on the basis of a position of a peak in amplitude of a one-dimensional spectrum $Xr(\omega, k)$ (K is the number of chirps). Since an amplitude peak of the target T2 is successfully sensed in the procedure indicated in the third example embodiment of the present invention, displacement of the target T2 is also successfully sensed by using the positional information.

Therefore, the processing flow of the object sensing device 1 (that detects a position by using two-dimensional Fourier transform) according to the third example embodiment of the present invention is suitable for the case of an object-sensing environment with much noise, in comparison with the processing flow of the object sensing device 1 (that detects a position by using one-dimensional Fourier transform) according to the second example embodiment of the present invention.

Therefore, the example embodiments are desired to properly use the processing flow of the object sensing device 1 according to the second example embodiment of the present invention and the processing flow of the object sensing device 1 according to the third example embodiment, depending on noise in an object-sensing environment.

(Observation Example)

An observation example is described.

Figure 14:
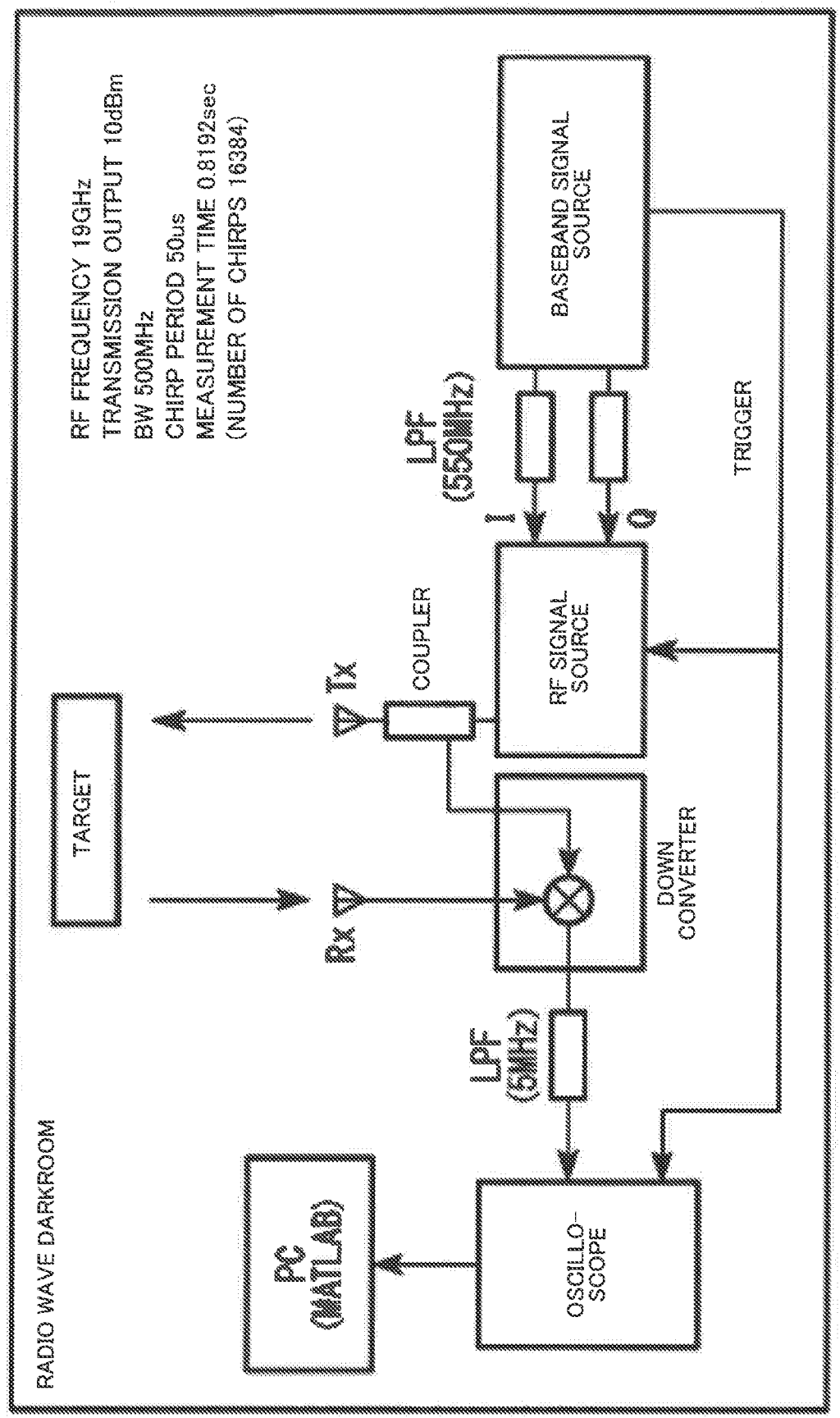
FIG. 14 is a diagram illustrating an example of radar constructed for performing observation according to the third example embodiment of the present invention.

For observation, radar was constructed in a radio wave darkroom by using a measurement device, as illustrated in FIG. 14.

A transmitter is constituted of a baseband signal source, an RF signal source, a low-pass filter, and a horn antenna. A data file of a baseband I-Q signal (chirp period 50 us, RF bandwidth 500 MHz, sampling rate 2 GS/s) was generated by using MATLAB (The MathWorks, Inc.) on a computer, and was downloaded on the baseband signal source from the computer. The baseband signal source outputs the baseband I-Q signal to an external IQ terminal of the RF signal source. The LPF having a cutoff frequency of 550 MHz is interposed between the baseband signal source and the RF signal source, in order to prevent an out-band signal from being input to the RF signal source. The RF signal source up-converts a baseband signal input to the external IQ terminal into an RF frequency (19 GHz), and outputs an RF signal from a connected transmission antenna toward a target. Note that, in the present invention, an RF frequency for use may not necessarily be limited to 19 GHz, and any frequency may be used. In the observation example, it is assumed that output power of a transmission RF signal is 10 dBm, but the output power of the transmission RF signal may be arbitrary.

A receiver is constituted of a horn antenna, a down converter, an oscilloscope, and an LPF. The down converter generates an IF signal by mixing an RF signal received by the horn antenna with a transmission RF signal acquired via a coupler. A frequency of an IF signal is substantially identical with a frequency shift $f_w$ generated from a delay time $\tau_0$ at a position $R_0$ at a time t=0, and is approximately 1 MHz or less in this case. In order to remove noise in an unnecessary band, the low-pass filter having a cutoff frequency of 5 MHz is interposed between the down converter and the oscilloscope. An IF signal is acquired by the oscilloscope (sampling rate 2 MS/s), and the acquired IF signal is transferred to a computer via a general purpose interface bus (GPIB). The computer analyzes the acquired IF signal by using an algorithm of performing the processing of the present invention implemented by MATLAB, and calculates a position and a state of displacement (vibration/shaking) of a target.

Note that, since the receiver itself has delay, a distance offset (error) occurs. This distance offset is obtained by through-measurement while a cable for linking a transmission antenna with a reception antenna is directly connected. The distance offset obtained in the measurement is 1.1 m, and the delay in the receiver is calibrated by subtracting a value of this distance offset from a measurement result.

Figure 15:
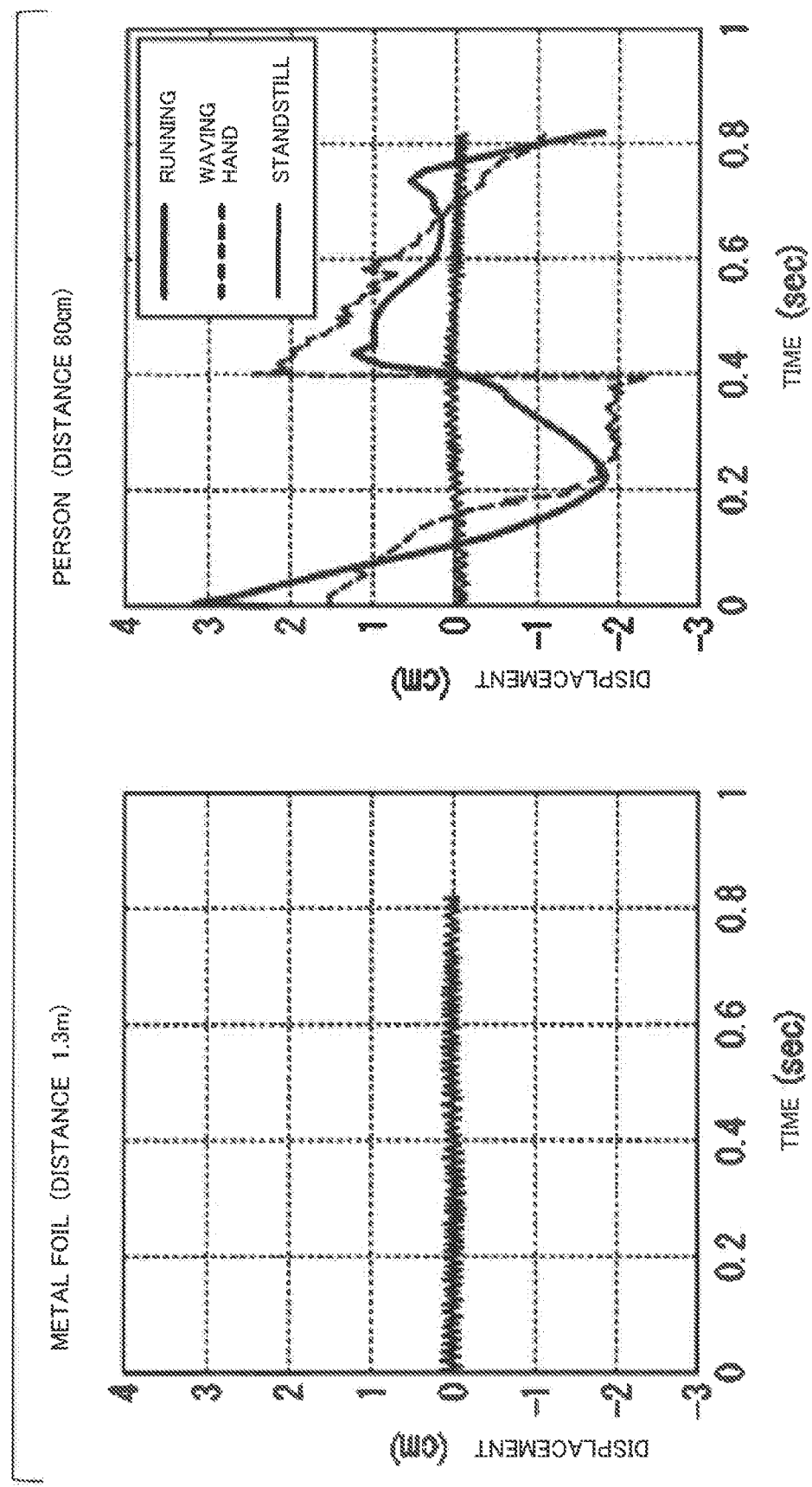
FIG. 15 is a diagram illustrating an observation result according to the third example embodiment of the present invention.

A position and a state of displacement of a target were measured by using an algorithm of performing the processing of the present invention. A target to be measured includes the following four, a metal box (measurement target 1), a person in a standstill state (measurement target 2), a person in a state of waving a hand (measurement target 3), and a person in a running state (measurement target 4). As in a measurement result illustrated in FIG. 15, no displacement was sensed for the metal box (measurement target 1) and the person in a standstill state (measurement target 2). Meanwhile, a displacement of about 4 to 5 cm in terms of a peak-to-peak value was sensed for the person in a state of waving a hand (measurement target 3) and the person in a running state (measurement target 4).

This indicates that the present invention is able to identify presence or absence of displacement of a target at a higher range resolution than in Fast-FMCW.

In the above, the object sensing device 1 according to the third example embodiment of the present invention has been described. The object sensing device 1 according to the third example embodiment of the present invention includes the transmitter 10 and the receiver 20. The transmitter 10 includes the irradiation unit 101, the control unit 102, and the storage unit 103. The spectrum calculation unit 207 calculates a two-dimensional spectrum $X(\omega, \Psi)$ of an IF signal x(t) by applying two-dimensional Fourier transform for each period. The position detection unit 203 detects a position $R_0$ and the velocity v of a target on the basis of a position of a peak in amplitude of a two-dimensional spectrum $X(\omega, \Psi)$. The displacement detection unit 204 detects displacement of a target on the basis of a phase $\angle Xr(\omega, \Psi)$ of a two-dimensional spectrum at a position $R_0$ and the velocity v of the target detected by the position detection unit 203.

With such a configuration, the object sensing device 1 is able to detect a moving body without using complicated processing or a special device in an environment with more noise.

Fourth Example Embodiment

An object sensing method according to a fourth example embodiment of the present invention is described. A main object of the object sensing method according to the fourth example embodiment of the present invention is to measure displacement (vibration) of a target and identify a "class" of the target on the basis of the displacement of the target.

Figure 16:
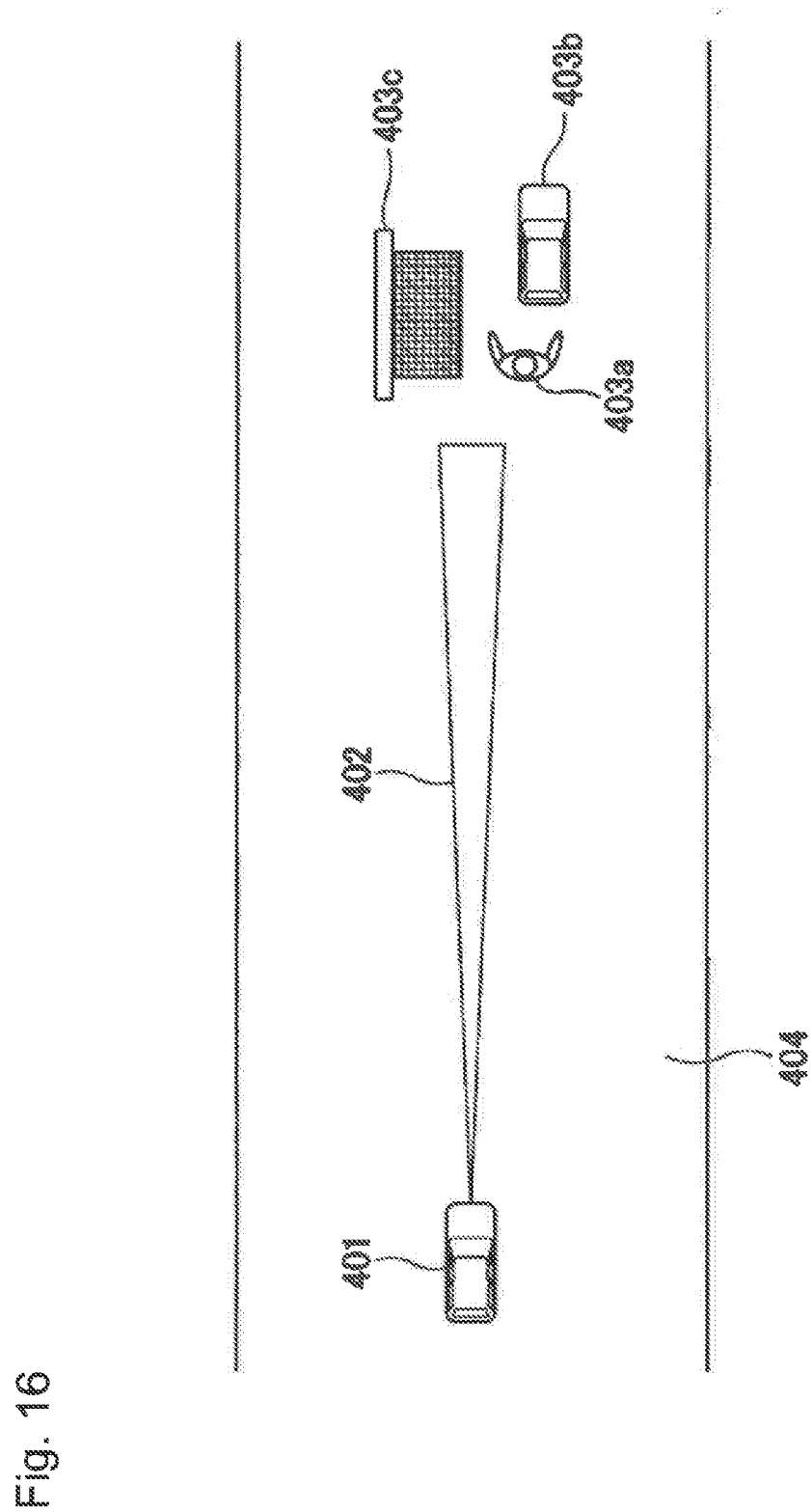
FIG. 16 is a diagram illustrating a configuration of an object sensing method according to a fourth example embodiment of the present invention.

The object sensing method according to the fourth example embodiment of the present invention is implemented by a moving body 401 that includes an object sensing device 1, and a target 403, as illustrated in FIG. 16. As the moving body 401, a vehicle such as an automobile or a train is assumed, but the moving body 401 may be any transportation equipment such as a flight vehicle or a watercraft. As the target 403, specifically, a pedestrian 403a, a machine 403b such as an automobile, an obstacle 403c, or the like is assumed, but an object other than the pedestrian 403a, the machine 403b such as an automobile, and the obstacle 403c may be the target 403. As a specific use place of the object sensing device 1, a road 404 is assumed, but the use place may be other than the road 404.

The object sensing device 1 mounted on the moving body 401 irradiates the target 403 with the RF transmission signal 402, receives a reflected wave from the target 403, and measures displacement of each target 403a, 403b, or 403c . . . , respectively, in accordance with the procedure described in the first through third example embodiments of the present invention.

On the basis of displacement of each target 403a, 403b, or 403c . . . measured in accordance with the procedure described in the first through third example embodiments of the present invention, the object sensing device 1 mounted on the moving body 401 identifies a class of each target 403a, 403b, or 403c . . . . For example, among the targets 403, the pedestrian 403a exhibits displacement (motion) with a frequency of not more than several Hz, which depends on a motion state. Further, among the targets 403, the machine 403b such as an automobile exhibits displacement (vibration) of about several tens of Hz, which depends on an operation state. Meanwhile, among the targets 403, the fixed obstacle 403c does not exhibit displacement (vibration) per se. In this manner, by use of the difference in a frequency of displacement (vibration) for each class of the target 403, the object sensing device 1 is able to identify a class (herein, the pedestrian 403a, the machine 403b, the obstacle 403c, or the like) of a target sensed by the object sensing device 1 by using a frequency of displacement of the target 403. Using a frequency of displacement for identification of a target is one example of an identification method, and, more generally, the object sensing device 1 may use a pattern of a time waveform of displacement for identification of a target.

Identifying a class of the target 403 as implemented in the present invention by using the object sensing device 1 mounted on the moving body 401, as well as sensing presence of the target 403 as implemented by using a conventional object sensing device, has an advantage leading to enhanced safety. For example, when the object sensing device 1 is able to identify the target 403 as being the pedestrian 403a, it is possible to predict that the pedestrian 403a takes a risky action such as crossing the road 404, and is possible to take a safety measure such as slowing down a movement speed of the moving body 401 in advance. When the target 403 is identified as being the fixed obstacle 403c, it is possible to predict that the obstacle 403c continues to exist at the same position. Further, when the target 403 is identified as being the machine 403b such as an automobile, it is possible to predict that the target 403 continues movement along the road. In this manner, class identification of the target 403 enables prediction of movement of a target, and thus, the prediction information may be used for a safe operation of the moving body 401.

Modification Example of Fourth Example Embodiment

In the object sensing method according to the fourth example embodiment of the present invention, the case where the object sensing device 1 is mounted on the moving body 401 is described. Meanwhile, the object sensing device 1 may be used in a state of being attached to fixing equipment 411, as in a modification example of the object sensing method according to the fourth example embodiment of the present invention illustrated in FIG. 17.

Figure 17:
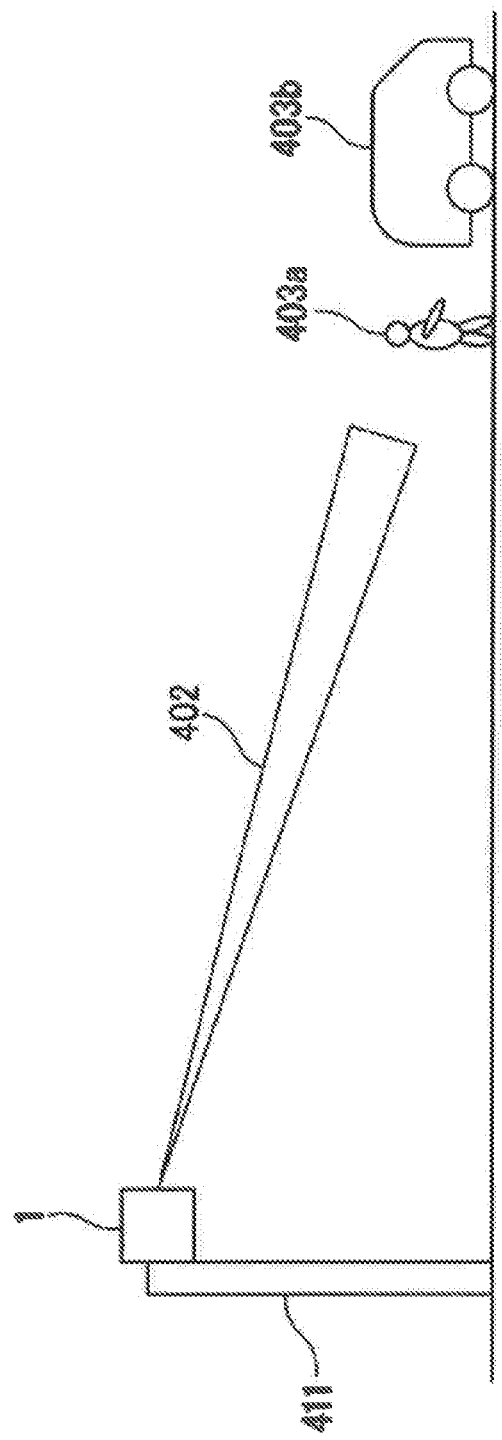
FIG. 17 is a diagram illustrating a configuration of an object sensing method according to a modification example of the fourth example embodiment of the present invention.

In the modification example of the object sensing method according to the fourth example embodiment of the present invention, the object sensing device 1 is provided in the vicinity of a specific area such as an intersection, a railroad crossing, or a premise of a building, and it is assumed that a class of the target 403 entering this specific area is identified. In FIG. 17, the pedestrian 403*a* and the machine 403*b* such as a vehicle are illustrated as one example of the target 403, but a class of the target 403 is not limited to the pedestrian 403*a* or the machine 403*b*. Similarly to the fourth example embodiment of the present invention, when a class of the target 403 can be identified, an identification result may be utilized in safety monitoring for a traffic risky area such as an intersection or a railroad crossing, or in crime prevention monitoring in a premise of a building.

Fifth Example Embodiment

An object sensing method according to a fifth example embodiment of the present invention is described. A main object of the object sensing method according to the fifth example embodiment of the present invention is to measure displacement (vibration) of a target and identify a "state" of the target on the basis of the displacement of the target.

Figure 18:
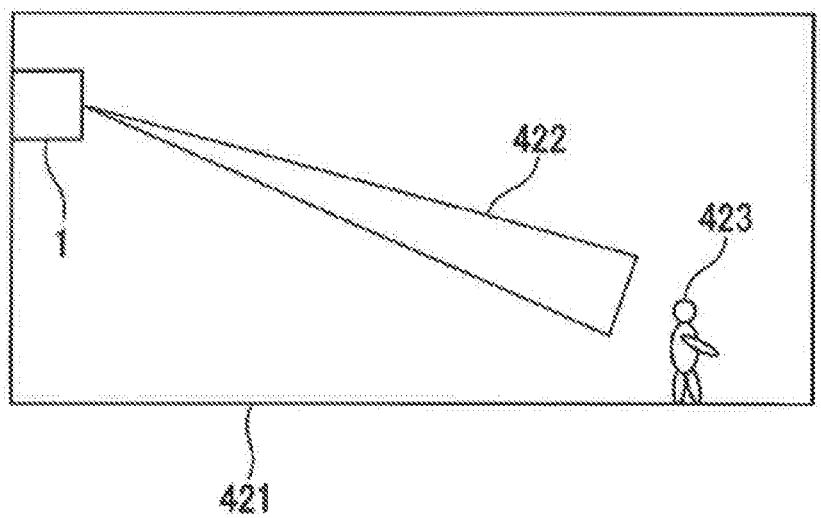
FIG. 18 is a diagram illustrating a configuration of an object sensing method according to a fifth example embodiment of the present invention.

In the object sensing method according to the fifth example embodiment of the present invention, an object sensing device 1 is attached to a wall of a room 421, as illustrated in FIG. 18. The object sensing device 1 irradiates a target 423 with the RF transmission signal 422, and receives a reflected wave from the target 423. The object sensing device 1 measures displacement of the target 423 in accordance with the procedure described in the first through third example embodiments of the present invention. In the fifth example embodiment of the present invention, the target 423 is assumed to be a person.

On the basis of displacement of the target (person) 423 measured in accordance with the procedure described in the first through third example embodiments of the present invention, the object sensing device 1 identifies a state of the target (person) 423. For example, the target (person) 423 in a state of being violent exhibits a larger frequency or amplitude of displacement than in a state of rest. By use of this characteristic of displacement, the object sensing device 1 is able to identify and monitor a state (being violent or rest) of the target (person) 423. State monitoring of the target (person) 423 is useful in both mental and physical health care for a patient or a prisoner in a public facility such as a hospital or a prison. Further, the object sensing device 1 may measure shaking (displacement) of the target (person) 423 due to heartbeat or breathing.

In FIG. 18, an example of an indoor space (the room 421) is described, but the object sensing method according to the fifth example embodiment of the present invention may be used in an outdoor public facility such as a station or an airport. A main object of use of the object sensing method according to the example embodiment of the present invention in an outdoor public facility is to prevent a crime, such as sensing an act of violence.

Modification Example of Fifth Example Embodiment

In the object sensing method according to the fifth example embodiment of the present invention described above, the target 423 is assumed to be a person. Meanwhile, the target may be a machine 424*a*, 424*b*, 424*c*, . . . , as in a modification example of the fifth example embodiment of the present invention illustrated in FIG. 19. In this case, on the basis of displacement (vibration) of the target (machine) 424*a*, 424*b*, 424*c*, . . . measured in accordance with the procedure described in the first through third example embodiments of the present invention, the object sensing device 1 predicts failure of the target (machine) 424*a*, 424*b*, 424*c*, . . . by using the fact that abnormality occurs in a vibrating state immediately before failure.

When vibration of the target (machine) 424*a*, 424*b*, 424*c*, . . . is measured by using a contact-type vibration sensor, it is necessary to prepare as many vibration sensors as the number of the targets (machines) 424*a*, 424*b*, 424*c*, . . . . This leads to a problem that attaching a contact-type vibration sensor causes much trouble when there are a large number of the targets (machines) 424*a*, 424*b*, 424*c*, . . .

Meanwhile, in the modification example of the fifth example embodiment of the present invention, the single object sensing device 1 is able to simultaneously measure displacement (vibration) of the plurality of targets (machines) 424*a*, 424*b*, 424*c*, . . . , respectively. Use of the object sensing device 1 has an advantage that no trouble of attaching a vibration sensor is caused.

Figure 19:
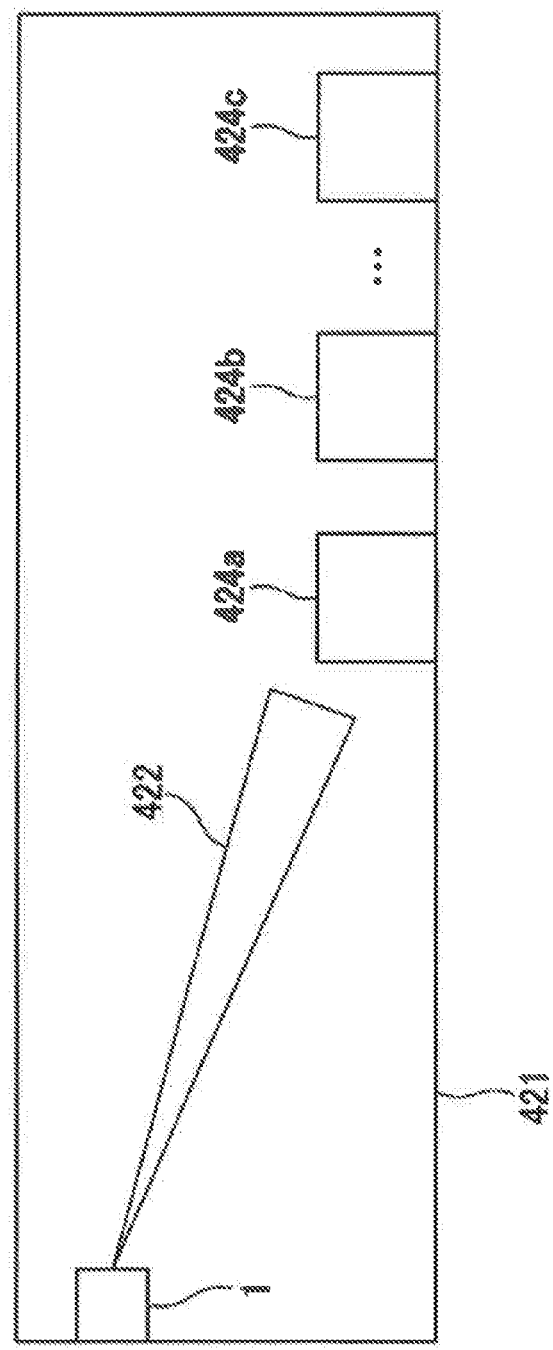
FIG. 19 is a diagram illustrating a configuration of an object sensing method according to a modification example of the fifth example embodiment of the present invention.

Note that, in FIG. 19, the targets (machines) 424*a*, 424*b*, 424*c*, . . . are placed in an indoor space (the room 421), but the targets 424*a*, 424*b*, 424*c*, . . . may be placed in an outdoor space. Further, the target measured by the object sensing device 1 may be a civil engineering structure such as a building or a bridge.

Sixth Example Embodiment

An automotive radar system according to a sixth example embodiment of the present invention is described.

Figure 20:
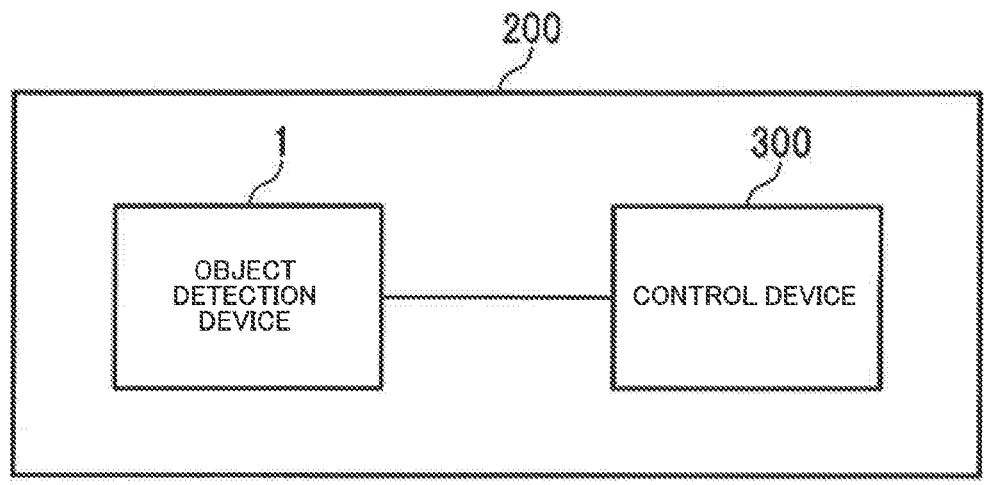
FIG. 20 is a diagram illustrating a configuration of an automotive radar system according to a sixth example embodiment of the present invention.

An automotive radar system 200 according to the sixth example embodiment of the present invention includes an object sensing device 1 and a control device 300, as illustrated in FIG. 20.

The automotive radar system 200 is mounted on an automobile.

The object sensing device 1 according to the sixth example embodiment of the present invention includes a transmitter 10 and a receiver 20.

The object sensing device 1 according to the sixth example embodiment of the present invention is the object sensing device 1 according to any one of the example embodiments of the present invention described above.

The object sensing device 1 detects a position and displacement of a target.

The object sensing device 1 outputs a detected position and displacement of a target to the control device 300.

The control device 300 acquires a position and displacement of a target from the object sensing device 1.

The control device 300 controls at least one of engine output and braking of an automobile on the basis of an acquired position and displacement.

For example, the control device 300 acquires information on a position and displacement indicating a person or another automobile as a target, and, when determining that the position is at a position securing a sufficient braking distance, lowers engine output, or the control device 300 decelerates an automobile by light braking. Further, the control device 300 acquires information on a position and displacement indicating a person or another automobile as a target, and, when determining that the position is as close as being risky unless an automobile is immediately stopped, lowers engine output and stops the automobile by sudden braking.

With such a configuration, the automotive radar system 200 is able to avoid collision between an automobile and a target.

Seventh Example Embodiment

A surveillance radar system according to a seventh example embodiment of the present invention is described.

Figure 21:
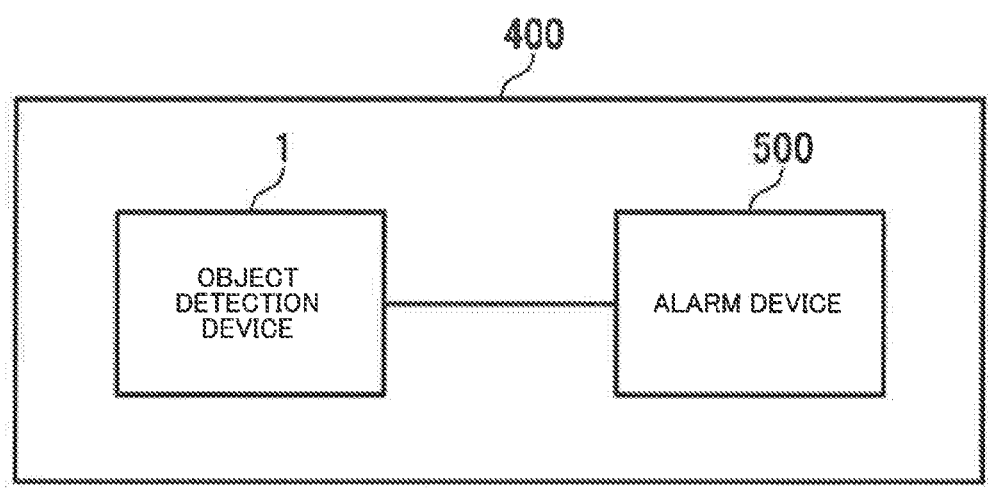
FIG. 21 is a diagram illustrating a configuration of a surveillance radar system according to a seventh example embodiment of the present invention.

A surveillance radar system 400 according to the seventh example embodiment of the present invention includes an object sensing device 1 and an alarm device 500, as illustrated in FIG. 21.

The surveillance radar system 400 is provided in, for example, a hospital room.

The object sensing device 1 according to the seventh example embodiment of the present invention includes a transmitter 10 and a receiver 20.

The object sensing device 1 according to the seventh example embodiment of the present invention is the object sensing device 1 according to any one of the example embodiments of the present invention described above.

The object sensing device 1 detects a position and displacement of a target.

The object sensing device 1 outputs a detected position and displacement of a target to the alarm device 500.

The alarm device 500 acquires a position and displacement of a target from the object sensing device 1.

The alarm device 500 outputs an alarm on the basis of an acquired position and displacement.

For example, the alarm device 500 acquires information on a position and displacement (motion) indicating a person (patient) as a target. When determining that the displacement is equal to or less than predetermined displacement for a given period of time or more, the alarm device 500 determines that the person hardly moves, the person is in cardiopulmonary arrest, or the like, and notifies another person of a bad physical condition of the person as a target by outputting an alarm to a hospital room, a nurse station, or the like. Further, in a home for elderly people or a home for an elderly person living alone, the object sensing device 1 may detect a target person passing out suddenly or not getting out of bed even after a regular wake-up time, from displacement and a position of the target person. Note that, as an alarm, sound or display, and further, emergency report through a communication line, notification to a portable terminal, or the like are conceivable. When a surveillance system by radar such as the surveillance radar system 400 is used, an image of a target person is not photographed, and thus, there is also an advantage of protecting individual's privacy.

With such a configuration, the surveillance radar system 400 is able to notify another person of a worsened physical condition or safety of a person and immediately contact a doctor or a nurse, and the doctor or the nurse is able to immediately perform a treatment on the person in a bad physical condition. The surveillance radar system 400 may surveil a prisoner or the like in a prison, in a manner similar to the above. Further, the surveillance radar system 400 may be used for crime prevention, in a manner such as determining displacement (motion) of a person in an indoor space, in an elevator, or the like, and contacting a security company when determining that the displacement of the person is large (the person is violent).

Note that the order of processes in the processing flow according to the example embodiment of the present invention may be changed, as far as processing is performed appropriately.

Each of the storage units 103, 206, and another storage unit according to the example embodiments of the present invention may be provided anywhere, as far as information is transmitted and received appropriately. Further, each of the storage units 103, 206, and another storage unit may store a plurality of pieces of data in a distributed manner, as far as information is transmitted and received appropriately.

The example embodiments of the present invention have been described. However, each of the object sensing device 1, the transmitter 10, and the receiver 20 described above may internally have a computer system. Then, a process of the above-described processing is stored in a computer-readable recording medium in a form of a program, and the above-described processing is performed by a computer reading and executing this program. Herein, a computer-readable recording medium refers to a magnetic disk, a magneto-optical disk, a CD-ROM, a DVD-ROM, a semiconductor memory, or the like. Further, this computer program may be distributed to a computer through a communication line, and the computer receiving this distribution may execute the program.

Further, the above-described program may implement a part of the aforesaid function. Furthermore, the above-described program may be a file that can implement the aforesaid function in combination with a program already recorded in a computer system, a so-called difference file (difference program).

Some example embodiments of the present invention have been described. However, these example embodiments are examples, and do not limit the scope of the invention. Addition, various types of omission, replacement, and modification may be made to these example embodiments within the scope not departing from the gist of the invention.

(Supplementary Note 1)

An object sensing device including a transmitter and a receiver, wherein the transmitter includes an irradiation unit that irradiates an RF transmission signal having a periodically swept frequency, and the receiver includes:

a reception unit that receives an RF reception signal that is a reflected wave of the RF transmission signal reflected by at least one target;

an IF signal generation unit that generates an IF signal by mixing the RF transmission signal with the RF reception signal;

a position detection unit that detects a position of the target, based on amplitude of a spectrum calculated from the IF signal for each period in which the frequency is swept; and a displacement detection unit that detects displacement of the target, based on a phase of a one-dimensional spectrum at the position of the target detected by the position detection unit, the phase of the one-dimensional spectrum being calculated from the IF signal for each of the period.

(Supplementary Note 2)

The object sensing device according to Supplementary note 1, wherein the position detection unit detects the position of the target, based on a peak in amplitude of the one-dimensional spectrum, by using the one-dimensional spectrum as the spectrum.

(Supplementary Note 3)

The object sensing device according to Supplementary note 1 or 2, wherein the displacement detection unit determines that displacement of the target is detected, when there is temporal change in the position of the target for each period of the IF signal, the position of the target being indicated by the phase of the one-dimensional spectrum.

(Supplementary Note 4)

The object sensing device according to any one of Supplementary notes 1 to 3, wherein the receiver includes a first spectrum calculation unit that calculates the one-dimensional spectrum of the IF signal by applying, to the IF signal, one-dimensional Fourier transform for each of the period.

(Supplementary Note 5)

The object sensing device according to Supplementary note 1, wherein the position detection unit detects the position of the target, based on a peak in amplitude of a two-dimensional spectrum calculated from the IF signal for each of the period, by using the two-dimensional spectrum as the spectrum, and the displacement detection unit detects displacement of the target, based on the phase of the one-dimensional spectrum at the position of the target detected by the position detection unit.

(Supplementary Note 6)

The object sensing device according to Supplementary note 5, wherein the receiver includes a second spectrum calculation unit that calculates the two-dimensional spectrum of the IF signal by applying, to the IF signal, two-dimensional Fourier transform for each of the period.

(Supplementary Note 7)

The object sensing device according to any one of Supplementary notes 1 to 6, wherein when the position detection unit detects positions of a plurality of the targets, the displacement detection unit calculates each displacement of the plurality of the targets, based on a phase of the one-dimensional spectrum corresponding to each position of the plurality of the targets.

(Supplementary Note 8)

An object sensing method of an object sensing device including a transmitter and a receiver, including:

irradiating an RF transmission signal having a periodically swept frequency;

receiving an RF reception signal that is a reflected wave of the RF transmission signal reflected by at least one target;

generating an IF signal by mixing the RF transmission signal with the RF reception signal;

detecting a position of the target, based on amplitude of a one-dimensional spectrum calculated from the IF signal for each period in which the frequency is swept; and detecting displacement of the target, based on a phase of the one-dimensional spectrum at the position of the target detected.

(Supplementary Note 9)

The object sensing method of the object sensing device according to Supplementary note 8, including detecting the position of the target, based on a peak in amplitude of the one-dimensional spectrum.

(Supplementary Note 10)

An object sensing method of an object sensing device including a transmitter and a receiver, including:

irradiating an RF transmission signal having a periodically swept frequency;

receiving an RF reception signal that is a reflected wave of the RF transmission signal reflected by at least one target;

generating an IF signal by mixing the RF transmission signal with the RF reception signal;

detecting a position of the target, based on amplitude of a two-dimensional spectrum calculated from the IF signal for each period in which the frequency is swept;

calculating a one-dimensional spectrum from the IF signal for each of the period; and detecting displacement of the target, based on a phase of the one-dimensional spectrum at the position of the target detected from the two-dimensional spectrum.

(Supplementary Note 11)

The object sensing method of the object sensing device according to Supplementary note 10, including detecting the position of the target, based on a position of a peak in the amplitude of the two-dimensional spectrum.

(Supplementary Note 12)

The object sensing method of the object sensing device according to any one of Supplementary notes 9 to 11, including identifying a class of the target, based on displacement of the target.

(Supplementary Note 13)

The object sensing method of the object sensing device according to any one of Supplementary notes 9 to 11, including identifying a state of the target, based on displacement of the target.

(Supplementary Note 14)

An automotive radar system including:

the object sensing device according to any one of Supplementary notes 1 to 7; and a control device, wherein the object sensing device outputs, to the control device, the position of the target detected by the position detection unit and displacement of the target detected by the displacement detection unit, and the control device controls at least one of engine output and braking, based on the position of the target and the displacement of the target.

(Supplementary Note 15)

A surveillance radar system including:

the object sensing device according to any one of Supplementary notes 1 to 7; and an alarm device, wherein the object sensing device outputs, to the alarm device, displacement of the target detected by the displacement detection unit, and the alarm device outputs an alarm, based on the displacement.

(Supplementary Note 16)

A program causing a computer of an object sensing device including a transmitter and a receiver, to execute:

irradiating an RF transmission signal having a periodically swept frequency;

receiving an RF reception signal that is a reflected wave of the RF transmission signal reflected by at least one target;

generating an IF signal by mixing the RF transmission signal with the RF reception signal;

detecting a position of the target, based on amplitude of a one-dimensional spectrum calculated from the IF signal for each period in which the frequency is swept; and detecting displacement of the target, based on a phase of the one-dimensional spectrum at the position of the target detected.

(Supplementary Note 17)

The program according to Supplementary note 16, causing to execute detecting the position of the target, based on a peak in amplitude of the one-dimensional spectrum.

(Supplementary Note 18)

A program causing a computer of an object sensing device including a transmitter and a receiver, to execute:

irradiating an RF transmission signal having a periodically swept frequency;

receiving an RF reception signal that is a reflected wave of the RF transmission signal reflected by at least one target;

generating an IF signal by mixing the RF transmission signal with the RF reception signal;

detecting a position of the target, based on amplitude of a two-dimensional spectrum calculated from the IF signal for each period in which the frequency is swept;

calculating a one-dimensional spectrum from the IF signal for each of the period; and detecting displacement of the target, based on a phase of the one-dimensional spectrum at a position of the target detected from the two-dimensional spectrum.

(Supplementary Note 19)

The program according to Supplementary note 18, causing to execute detecting a position of the target, based on a peak in amplitude of the two-dimensional spectrum.

(Supplementary Note 20)

The program according to any one of Supplementary notes 16 to 19, causing to execute identifying a class of the target, based on displacement of the target.

(Supplementary Note 21)

The program according to any one of Supplementary notes 16 to 19, causing to execute identifying a state of the target, based on displacement of the target.

This application is based upon and claims the benefit of priority from Japanese Patent Application No. 2016-107203, filed on May 30, 2016, the disclosure of which is incorporated herein.

INDUSTRIAL APPLICABILITY

The present invention is applicable to a use for which it is necessary to detect a moving body without using complicated processing or a special device.

REFERENCE SIGNS LIST

1 Object sensing device
10 Transmitter
20 Receiver
101 Irradiation unit
102, 205 Control unit
103, 206 Storage unit
200 Automotive radar system
201 Reception unit
202 IF signal generation unit
203 Position detection unit
204 Displacement detection unit
207 Spectrum calculation unit
300 Control device
400 Surveillance radar system
500 Alarm device

What is claimed is:

1. An object sensing device comprising:

a transmitter and a receiver, wherein the transmitter includes an irradiator configured to irradiate a Radio Frequency transmission signal having a periodically swept frequency to at least one target, and the receiver includes:

a receptor configured to receive a Radio Frequency reception signal being a reflected wave of the Radio Frequency transmission signal irradiated to the target by the irradiator, an Intermediate Frequency signal generator configured to generate an Intermediate Frequency signal by mixing the Radio Frequency transmission signal with the Radio Frequency reception signal, a position and velocity detector configured to detect a position of the target, based on amplitude of a two-dimensional spectrum calculated from the Intermediate Frequency signal for each period in which the frequency is swept, and a displacement detector configured to detect displacement of the target, based on a phase of a two-dimensional Fourier transform at the position and velocity of the target being detected by the position and velocity detector, the phase of the two-dimensional Fourier transform being calculated from the Intermediate Frequency signal for each of the period.

2. The object sensing device according to claim 1, wherein the receiver includes a second spectrum calculator configured to calculate the two-dimensional spectrum of the Intermediate Frequency signal by applying, to the Intermediate Frequency signal, two-dimensional Fourier transform for each of the period.

3. The object sensing device according to claim 1, wherein, when there is a plurality of the targets, the displacement detector calculates each displacement of the plurality of the targets, based on a phase of the two-dimensional spectrum at a position of a peak in amplitude of the two-dimensional spectrum.

4. An object sensing method for an object sensing device including a transmitter and a receiver, comprising:

irradiating a Radio Frequency transmission signal having a periodically swept frequency;

receiving a Radio Frequency reception signal being a reflected wave of the Radio Frequency transmission signal reflected by at least one target;

generating an IF signal by mixing the Radio Frequency transmission signal with the Radio Frequency reception signal;

detecting a position and velocity of the target, based on amplitude of a two-dimensional spectrum calculated from the IF signal for each period in which the frequency is swept;

calculating a two-dimensional Fourier transform from the Intermediate Frequency signal for each of the period; and detecting displacement and velocity of the target, based on a phase of the two-dimensional Fourier transform at the position of the target being detected from the two-dimensional Fourier transform.

5. The object sensing method for the object sensing device according to claim 4, further comprising
identifying a class of the target, based on displacement of the target.

6. The object sensing method for the object sensing device according to claim 4, further comprising
identifying a state of the target, based on displacement of the target.

* * * * *